United States Patent [19]
Liu et al.

[11] Patent Number: 5,238,940
[45] Date of Patent: Aug. 24, 1993

[54] COMPOSITIONS FOR PHOTODYNAMIC THERAPY

[75] Inventors: Daniel Liu; Frank Jiang; John Hobbs, all of Vancouver, Canada

[73] Assignee: Quadra Logic Technologies Inc., Vancouver, Canada

[21] Appl. No.: 768,810

[22] Filed: Sep. 30, 1991

Related U.S. Application Data

[63] Continuation-in-part of Ser. No. 498,042, Mar. 22, 1990, Pat. No. 5,053,423.

[51] Int. Cl.$^5$ ..................... A61K 31/40; C07D 487/22
[52] U.S. Cl. ........................................ 514/410; 514/2; 514/43; 540/145
[58] Field of Search ................. 514/2.43, 410; 540/145

[56] References Cited

U.S. PATENT DOCUMENTS

| | | | |
|---|---|---|---|
| 4,268,947 | 5/1981 | Hile | 29/451 |
| 4,485,806 | 12/1984 | Akers | 128/1 R |
| 4,500,507 | 2/1985 | Wong | 424/1.1 |
| 4,512,762 | 4/1985 | Spears | 604/21 |
| 4,577,636 | 3/1986 | Spears | 128/654 |
| 4,675,338 | 6/1987 | Bommer et al. | 514/410 |
| 4,727,027 | 2/1988 | Wiesenhahn et al. | 435/173 |
| 4,748,120 | 5/1988 | Wiesenhahn et al. | 435/173 |
| 4,753,958 | 5/1988 | Weinstein et al. | 514/410 |
| 4,883,790 | 11/1989 | Levy et al. | 540/145 |
| 5,053,423 | 10/1991 | Liu | 514/410 |
| 5,093,349 | 3/1992 | Pandey et al. | 514/410 |
| 5,095,030 | 3/1992 | Levy et al. | 514/410 |

FOREIGN PATENT DOCUMENTS

| | | |
|---|---|---|
| 0161606 | 11/1985 | European Pat. Off. . |
| 0276121 | 7/1988 | European Pat. Off. . |
| WO90/02747 | 3/1990 | PCT Int'l Appl. . |

OTHER PUBLICATIONS

Dougherty et al., "Porphyrin Photosensitization" Kessel et al., editors, (1983) Plenum Press, pp. 3-13.
Gregorie et al., Ann. Surg. (1968) 167:827–829.
Diamond et al., Lancet (1972) 2:1175–1177.
Dougherty et al., Cancer Research (1978) 38:2628–2635.
Dougherty et al., "The Science of Photo Medicine" (1982) Regan & Parish, editors, pp. 625–638.
Dougherty et al., "Cancer: Principles and Practice of Oncology" (1982) Devita et al., editor, pp. 1836–1844.
Mew et al., J. Immunol. (1983) 130(3):1473–1477.
Mew et al., Cancer Research (1985) 45:4380–4386.
Oseroff et al. Proc. Natl. Acad. Sci. USA (1986) 83:8744–8748.
Steele et al., Cancer Immunol. Immunotherapy (1988) 26(2): 125–131.
Wat et al., Prog. Clin. Biol. Res. (1984) 170:351–359.
Levy et al., Lasers Surg. Meth. (1985) 5(2):141.
Weishaupt et al., Cancer Research (1976) 36:2326–2329.
Dougherty et al., "Porphyrin Localization and Treatment of Tumors" (1984) pp. 301–314.
Dougherty CRC Critical Reviews in Oncology/Hematology (1984) 2(2):83–116.
Richter et al., J. Natl. Cancer Inst. (1987) 79(6):1327–1332.
Krinick et al., Adv. Photochemotherapy (1988) 997:70–83.
Morgan et al., J. Chem. Soc. Chem. Commun. (1984) pp. 1047–1048.
Inamura et al., Biochim. Biophys. Acta (1988) 932:335–344.

Primary Examiner—Richard L. Raymond
Attorney, Agent, or Firm—Morrison & Foerster

[57] ABSTRACT

Methods to prepare intermediates for the conjugation of active ingredients to hydrophilic carriers are described. The polyhydroxylated carriers are first derivatized to convert the hydroxyls to leaving groups and then reacted with an alkylene diamine in the presence of a reducing agent. The resulting derivatized carrier can then be coupled to substituents containing carboxyl groups in the presence of dehydrating agents.

8 Claims, 16 Drawing Sheets

COMPOSITIONS FOR PHOTODYNAMIC THERAPY

This is a continuation-in-part of U.S. Ser. No. 498,042, filed Mar. 22 1990, now U.S. Pat. No. 5,053,423.

TECHNICAL FIELD

The present invention relates to methods to prepare pharmaceutical compositions useful in photodynamic therapy. More specifically, the invention concerns conjugates of porphyrin-type photosensitizers with hydrophilic polymers as active ingredients in compositions which can be used to effect the destruction or impairment of suitable target moieties such as cancer cells and viruses.

BACKGROUND ART

The use of porphyrin-type photosensitizers for the selective destruction of, for example, cancer cells in animal subjects has been known for several decades. The initial work utilized a mixture of porphyrins prepared from hematoporphyrin by treatment of this starting material with a mixture of sulfuric and acetic acids to result in a composition known specifically as hematoporphyrin derivative (HPD). (See, for example, "Porphyrin Photosensitization" Kessel, D., et al., eds. (1983) Plenum Press.)

HPD and related porphyrin-type photosensitizers appear to localize in malignant cells at the expense of normal tissues. The cells in which the HPD has been accumulated can then be irradiated using light of an appropriate wavelength absorbed by the HPD. When irradiated, the HPD and related photosensitizers have two properties which make them useful. First, when irradiated with the appropriate wavelength, the compounds are capable of fluorescence and can thus be used to detect cells in which they are accumulated (see, for example, Kessel, D., et al., (supra); Gregory, H. B., Jr., et al., Ann Surg (1968) 167:827–829). Second, HPD and its relatives discussed below are useful in therapeutic methods because when irradiated with visible light, a cytotoxic affect on the cells in which they are localized is exerted (see, for example, Diamond, I., et al., Lancet (1972) 2:1175–1177; Dougherty, T. J., et al., Cancer Research (1978) 38:2628–2635; Dougherty, T. J., et al., "The Science of Photomedicine" (1982), J. D. Regan and J. A. Parrish, eds.; Dougherty, T. J., et al., Cancer: Principles and Practices of Oncology (1982) B. T. DeVita Jr. et al., eds.) An improved photosensitizer which is prepared from HPD by adjustment of pH to cause aggregation and recovery of the aggregate is disclosed in U.S. Pat. No. 4,649,151, incorporated herein by reference. The "purified" form of the mixture is called dihematoporphyrin ether (DHE) in the patent and is marketed under the trademark Photofrin ® II. This has been used, as described in U.S. Pat. No. 4,649,151 in a manner completely analogous to HPD.

Other porphyrin-type photosensitizers have also been reported, including various chlorophyll derivatives derived from both bacteria and higher plants. A group of compounds of particular interest is that described as green porphyrins (Gp) in copending U.S. application 414,201 filed Sep. 28, 1989, now U.S. Pat. No. 5,095,030 assigned to the same assignee, and incorporated herein by reference. These compounds are so designated because they absorb light at longer wavelengths than that absorbed by hematoporphyrin derivative or its related compounds, and therefore these porphyrins appear green in white light. The green porphyrins are derived from protoporphyrin-IX by a reaction with a single acetylenic dienophile in a Diels-Alder reaction, and optional subsequent rearrangement and/or reduction. A subset of green porphyrins, designated herein benzoporphyrin derivatives (BPD) are particularly useful among this group.

All of the porphyrin-type photosensitizing compounds described in the literature are generally useful in the same manner as hematoporphyrin derivative as set forth in the above-cited art. In addition, however, to in vivo therapeutic and diagnostic protocols for tumors, as described above, these compounds can be used in other in vivo and in vitro applications. For example, these photosensitizers are useful in the detection of atherosclerotic plaques as described in U.S. Pat. Nos. 4,512,762 and 4,577,636. U.S. Pat. Nos. 4,500,507 and 4,485,806 describe the use of radiolabeled porphyrin compounds, including HPD, for tumor imaging. U.S. Pat. No. 4,753,958 describes the use of topical applications of porphyrin sensitizers for diagnosis and treatment of skin diseases. U.S. Pat. No. 4,748,120 describes the use of photosensitizers in the treatment of whole blood or blood components to rid them of infectious agents. Photochemical decontamination treatment of blood and components is also described in U.S. Pat. No. 4,727,027 where the photosensitizer is furocoumarin and its derivatives, rather than porphyrin-type materials. In addition, viruses are inactivated in therapeutic protein compositions in vitro as disclosed in U.S. Pat. No. 4,268,947.

For the administration of the porphyrin related photosensitizers in in vivo applications, various pharmaceutical compositions have been suggested. In one approach, the photosensitizing drug was coupled to antibodies which putatively enhance the ability of the drug to localize in the desired target cell. For instance, HPD was coupled to antibodies directed to the murine myosarcoma cell line M1 as described by Mew, D., et al., J Immunol (1983) 130:1473–1477. HPD was also conjugated to CAMAL-1 antibodies which are directed to a human leukemia antigen (Mew, D., et al., Cancer Research (1985) 45:4380–4386). The conjugation of chlorin $e_6$ to anti T-cell monoclonal antibody was described by Oseroff, A. R., et al., Proc Natl Acad Sci USA (1986) 83:8744–8748.

The use of liposomes or lipoproteins as pharmaceutical excipients for hematoporphyrins and related compounds has also been described. In addition, conventional pharmaceutical excipients have been used; however, the ability to administer significant amounts of photosensitizing drug in a relatively small volume of composition is impaired by the intrinsic water insolubility of most of these compounds. The present invention provides a means to solubilize these photosensitizers in a manner which permits ready administration while having no adverse effects on the accumulation on these materials in target cells or viruses or on the ability of the photosensitizing agent to absorb the appropriate radiation and exert cytotoxic effects or be detectable by fluorescence.

Disclosure of the Invention

The invention provides pharmaceutical compositions which are useful in solubilizing porphyrin-type photosensitizers and in providing a means for effective administration of these drugs, as well as facilitating the linkage of these photosensitizers into a complex with a targeting agent. The photosensitizing porphyrin-type compounds are conjugated to a hydrophilic polymer in a suitable ratio of photosensitizer to polymer to permit the solubilization of the sensitizer and effective administration thereof; in addition the polymer can further be coupled to a targeting moiety to result in a conjugate wherein both targeting agent and photosensitizer retain maximal activity.

In another, more general sense, this invention provides pharmaceutical compositions useful for facilitating the targeted delivery of pharmaceutical agents generally. These compositions include an active pharmaceutical agent conjugated to a hydrophilic polymer together with a targeting moiety.

The products of the invention method are pharmaceutical compositions useful in photodynamic therapy or related methodologies, which compositions contain as an active ingredient a conjugate of a porphyrin-type photosensitizer with a water soluble, multifunctional hydrophilic polymer. The ratio of photosensitizer to polymer will be variable depending on the particular circumstances, and generally can vary from ~1:1 to 500:1. Particularly useful forms of hydrophilic polymers include low molecular weight polysaccharides, polyvinyl alcohol, polyallyl amine, and hydroxylated esters of polymethyl acrylic acid or polyacrylic acid.

The products of the invention method also include pharmaceutical compositions which contain complexes wherein the water soluble, multifunctional, hydrophilic polymers such as those described above are conjugated both to a photosensitizing drug derived from porphyrin and a targeting agent which effects homing of the complex to the desired cell or tissue. Such targeting agents include antibodies or fragments thereof, receptor ligands, and generally any ligand which specifically binds to a surface characteristic of the target cells.

More generally, the products of the invention method are pharmaceutical compositions which contain complexes wherein a water soluble, multifunctional, hydrophilic polymer such as those described above is conjugated both to an active drug and a targeting agent which effects homing of the complex to a desired cell or tissue where the drug's action is desired. Such targeting agents include antibodies or fragments thereof, receptor ligands, and generally any ligand which specifically binds to a surface characteristic of the target cells.

BRIEF DESCRIPTION OF THE DRAWINGS

FIG. 2 is a flow diagram for the coupling of photosensitizer to PVA.

FIG. 3A relates to BPD-MA and its conjugate; FIG. 3B relates to DHE and its conjugate.

FIG. 6 outlines the conjugation of antibody to carrier.

MODES FOR CARRYING OUT THE INVENTION

The invention employs conjugates of hydrophilic polymers with photosensitizing compounds which are porphyrins or porphyrin related. One major advantage of such conjugates, besides conferring solubility on the drug, is the facilitation of formation of complexes which contain both photosensitizing drug and targeting agent. In addition to solubilizing both these components, the carrier provides a "backbone" matrix to which each of these components can be bound independently without significant loss of activity. A wide variety of each of these components is available for use in the compositions of the invention. In addition, the conjugates both of drug and carrier alone and those including homing moieties such as antibodies or receptor ligands can be further reacted with additional components such as labels or other cytotoxic elements. In other modes, the invention employs these aspects to conjugate and deliver other active agents beyond the photosensitizers.

The Photosensitizer

The photosensitizers of the invention are porphyrin-type photosensitizers as are generally known and employed in the art. A number of references describing some of these compounds are cited in the background section above. By far the largest body of experimental work has been conducted on the improved form of hematoporphyrin derivative (HPD) which is a composition whose preparation is described in the above cited Dougherty U.S. Pat. No. 4,649,151. This material is referred to herein for convenience in the same manner as described in that patent, as dihematoporphyrin ether (DHE) although it is understood that the mixture prepared as described contains numerous additional components many of which are active photosensitizers. Thus, as used herein, "DHE" refers specifically to the described mixture rather than an individual compound or mixture of compounds limited to dihematoporphyrin ethers per se.

Figure 1:
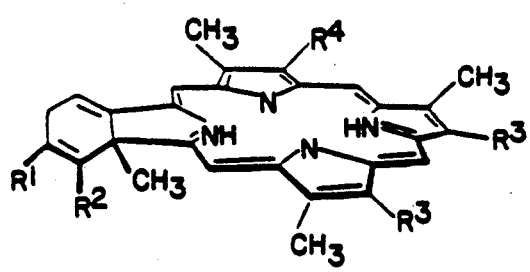
FIGS. 1-1 through 1-6 show the generic structures of green porphyrins, one group of photosensitizers useful in the conjugates of the invention.

An additional group of compounds which has been found extremely useful in photodynamic therapy and related methodologies is the green porphyrin (Gp) group having the basic structure outlined in FIG. 1. These compounds are prepared by a Diels-Alder reaction with the substrate related to protoporphyrin-IX, resulting in an adduct to the A or B ring as shown. As FIG. 1 shows, the direct product of the addition, shown as formulas 1 and 2 contains a fused hydrobenzene ring wherein the diene is unconjugated. Rearrangement of the compound of formulas 1 or 2 to the compounds of formulas 3 or 4 results in conjugation of the pi-bonds in the fused cyclohexadiene. The compounds of general formulas 3 and 4 are referred to herein as benzoporphyrin derivatives or "BPD." These compounds are named specifically as the compounds of formulas 3 and 4 appear to be the most useful in most applications.

The compounds of formulas 5 and 6 represent reduction products of the compounds of formulas 1-4 which retain an exocyclic double bond in the hydrobenzene nucleus. The preparation of some of these compounds was described in Morgan, A. R., et al., J Chem Soc Chem Commun (1984), pp. 1047-1048, and by Pangka, B. S., et al., *J Org Chem* (1986) 51:1094. The general techniques for Diels-Alder reaction with an acetylene-derived dieneophile and subsequent rearrangement and reduction of the products is described in these papers.

As to the indicated substituents in the compounds of FIG. 1, the permissible embodiments to retain effectiveness are quite numerous. In general, $R^1$ and $R^2$ are each, independently, moderate electron-withdrawing substituents, and are, most commonly, carbalkoxy, or alkyl or aryl sulfonyl, or any other activating substituents, which are not sufficiently electron-withdrawing to result in reaction with both A and B rings rather than reaction with only one, such as cyano or —CONR$^5$CO— wherein $R^5$ is aryl or alkyl. One of $R^1$ and $R^2$ may optionally be H while the other is an electron withdrawing substituent of sufficient strength to facilitate the reaction.

In summary, each $R^1$ and $R^2$ is independently selected from the group consisting of carbalkoxy (2-6C), alkyl (1-6C) sulfonyl, aryl (6-10C); cyano; and —CONR$^5$CO— wherein $R^5$ is aryl (6-10C) or alkyl (1-6C). In general, carboxy is, as conventionally defined, —COOH and carbalkoxy is —COOR, wherein R is alkyl; carboxy alkyl refers to the substituent —R'—COOH wherein R' is alkylene; carbalkoxy alkyl refers to —R'—COOR wherein R' and R are alkylene and alkyl respectively. Alkyl is a saturated straight or branched chain hydrocarbyl of 1-6 carbon atoms such as methyl, n-hexyl, 2-methylpentyl, t-butyl, n-propyl, and so forth. Alkylene is as alkyl except that the group is divalent. Aryl sulfonyl or alkyl sulfonyl moieties have the formula SO$^2$R wherein R is alkyl as above-defined, or is aryl, wherein aryl is phenyl optionally substituted with 1-3 substituents independently selected from halo (fluoro, chloro, bromo or iodo), lower alkyl (1-4C) or lower alkoxy (1-4C). In addition, one or both $R^1$ of $R^2$ can itself be aryl—i.e., phenyl optionally substituted as above-defined.

As shown in FIG. 1, the adduct formed by the reaction of $R^1$—C≡C—$R^2$ with the protoporphyrin-IX ring system ($R^3$ is a protected form of 2-carboxyethyl such as 2-carbomethoxy ethyl or 2-carboethoxy ethyl; $R^4$ is CH=CH$_2$) are compounds of the formulas 1 and 2 wherein the compound in formula 1 results from addition to the A ring and formula 2 results from addition to the B ring. In these resulting products of formulas 1 and 2, $R^4$ remains CH=CH$_2$; however this vinyl group is readily derivatized to other embodiments of $R^4$ by addition to or oxidation of the vinyl ring substituent of ring B in formula 1 or ring A in formula 2. The addition or oxidation products can be further substituted if the added substituents are functional leaving groups—for example —Br may be substituted by —OH, —OR (R is alkyl 1-6C as above), or —NH$_2$, —NHR, —NR$_2$, etc. In preferred embodiments, one of the added substituents is hydrogen, and the other is selected from the group consisting of halo (fluoro, chloro, bromo or iodo), hydroxy, lower alkoxy, amino or an amide, sulfhydryl or an organo-sulfide or can be, itself, hydrogen. Addition to the vinyl group does not appreciably change the absorption spectrum of the resulting compound. The product of the Markovnikov addition of water provides a substituent structure analogous to the hematoporphyrin ring system at the relevant ring. Thus, the compounds of the invention include various groups as $R^4$, including substituents which provide additional porphyrin or porphyrin-related ring systems, as will be further described below.

$R^3$ in protoporphyrin-IX is 2-carboxyethyl (—CH$_2$CH$_2$COOH). However, the nature of $R^3$ (unless it contains a pi-bond conjugated to ring pi-bond), is ordinarily not relevant to the progress of the Diels-Alder reaction or to the effectiveness and absorption spectrum of the resulting product. $R^3$ can thus be, for example, lower alkyl (1-4C), or omega-carboxyalkyl (2-6C) or the esters or amides thereof. The $R^3$ substituent may also be substituted with halogen as above-defined, or with other nonreactive substituents. However, as the convenient starting materials for the Gp compounds of the invention are the naturally occurring porphyrins, the preferred substituents for $R^3$ are CH$_2$CH$_2$COOH or —CH$_2$CH$_2$COOR, wherein R is alkyl (1-6C).

It should be noted that while the nature of the $R^3$ substituent does not ordinarily influence the course of the Diels-Alder reaction by altering the nature of the diene substrate, derivatization may be necessary to promote the reaction by providing suitable solubility characteristics or to prevent interference with the reaction. Thus, the Diels-Alder reactions described by Morgan et al. and by Pangka et al. utilized the dimethyl ester of protoporphyrin-IX as a substrate in order to prevent interference with the reaction by the free carboxyl group and to provide suitable solubility characteristics.

In certain BPD compounds of the invention (formulas 3 and 4 wherein both $R^3$ are initially —CH$_2$CH$_2$COOR, and $R^1$ and $R^2$ are —COOR), it has been found advantageous to hydrolyze or partially hydrolyze the esterified carboxy group in —CH$_2$CH$_2$COOR. The hydrolysis occurs at a much faster rate than that of the ester groups of $R^1$ and $R^2$, and the solubility characteristics of the resulting compounds are more desirable than those of the unhydrolyzed form. Hydrolysis results in the diacid or monoacid products (or their salts).

In further detail, concerning formulas 3 and 4, the hydro-monobenzoporphyrins which directly result from the Diels-Alder reaction described in the cited references can also be isomerized as therein described (see Morgan et al. and Pangka et al. (supra)) to compounds of formulas shown as 3 and 4 of FIG. 1 by treatment with suitable reagents such as triethylamine (TEA) in methylene chloride or 1,5-diaza bicyclo [5.4.0] undec-5-ene (DBU). The stereochemistry of the product is determined by the choice of reagent.

The depictions of compounds 3 and 4 in FIG. 1 do not show the relative position of the exocyclic methyl group (ring A of formula 3 and ring B of formula 4) with respect to the $R^2$ substituent. It has been found by these authors that rearrangement using TEA gives cis geometry for the angular methyl group and $R^2$, while treatment with DBU results in the trans product. This cis product is evidently kinetically controlled since treatment of the cis product with DBU results in a further rearrangement to trans stereochemistry. Thus, formulas 3 and 4 of FIG. 1 show the rearranged products generically, from either TEA or DBU catalyzed rearrangement in rings A and B respectively.

In addition, the Diels-Alder products can be selectively reduced by treating with hydrogen in the presence of palladium on charcoal to give the saturated ring analogs, shown as formulas 5 and 6 in FIG. 1, corresponding to the respective Diels-Alder products of rings A and B. These reduced products are less preferred embodiments, and are less useful in the method of the invention than the compounds of formulas 1-4.

The description set forth above with respect to the compounds of formulas 1 and 2 concerning derivatization by conversion of the remaining vinyl substituent ($R^4$) and with respect to variability of —$R^3$ applies as well to the compounds of formulas 3, 4, 5 and 6.

The compounds of formulas 3 and 4 (BPD), and especially those which have hydrolyzed and partially hydrolyzed carbalkoxy groups in $R^3$, are most preferred. Porphyrin related compounds in general, and, in particular, these BPD embodiments which contain —COOH may be prepared as the free acid or in the form of salts with organic or inorganic bases.

It will be noted that many of the compounds at east one chiral center and therefore exist as optical isomers. The green porphyrins and other porphyrins useful in the invention include compounds having both configurations of the chiral carbons, whether the compounds are supplied as isolates of a single stereoisomer or are mixtures of enantiomers and/or diastereomers. Separation of mixtures of diastereomers may be effected by any conventional means; mixtures of enantiomers may be separated by usual techniques of reacting them with optically active preparations and separating the resulting diastereomers.

For the green porphyrins, the reaction products may be unseparated mixtures of A and B ring additions, e.g., mixtures of formulas 1 and 2 or 3 and 4 or 5 and 6. Either the separated forms—i e., formula 3 alone or 4 alone, or mixtures in any ratio may be employed in the methods of therapy and diagnosis set forth herein Four particularly preferred compounds useful in the conjugates herein are collectively designated benzoporphyrin derivative (BPD) as they are forms of Gp having the formula 3 or 4. In these compounds $R^1$ and $R^2$ are carbalkoxy and $R^3$ is carbalkoxy ethyl. The preferred forms are hydrolyzed or partially hydrolyzed wherein one or both of the protected carboxyl groups of $R^3$ are hydrolyzed. The ester groups at $R^1$ and $R^2$ hydrolyze relatively so slowly that these can be retained in esterified form.

For purposes of the following description, $R^3$ is —$CH_2CH_2COOR^{3\,\prime}$. Each $R^{3\,\prime}$ is H in preferred compound BPD—DA, $R^1$ and $R^2$ are carbalkoxy, and derivatization is at ring A; BPD—DB is the corresponding compound wherein derivatization is at ring B. BPD-MA represents the partially hydrolyzed form of BPD-DA, and BPD-MB, the partially hydrolyzed form of BPD-DB. Thus, in these, latter compounds, $R^1$ and $R^2$ are carbalkoxy, one $R^3$ is H and the other $R^{3\,\prime}$ is alkyl (1-6C). The compounds of formulas BPD-MA and BPD-MB may be homogeneous wherein only the C ring carbalkoxy ethyl or only the D ring carbalkoxy ethyl is hydrolyzed, or may be mixtures of the C and D ring substituent hydrolysates. In addition, mixtures of any two or more of BPD—MA, —MB, —DA and —DB may be employed in the method of the invention.

Certain other embodiments wherein $R^4$ is other than vinyl or wherein $R^3$ is a non-native substituent are possible as well.

For example, each $R^3$ can be independently, in addition to carboxyethyl, carboxyalkyl generally (2–6C) or a salt, amide, ester or acylhydrazone thereof, or alkyl (1–6C).

With respect to $R^4$ in addition to $CHCH_2$, this can be $CHOR^{4\prime}$, —CHO, —COOR$^{4\prime}$, CH(OR$^{4\prime}$)CH$_3$, CH(OR$^{4\prime}$)CH$_2$OR$^{4\prime}$, —CH(SR$^{4\prime}$)CH$_3$, —CH(NR$^{4\prime}_2$)CH$_3$, —CH(CN)CH$_3$, —CH(COOR$^{4\prime}$)CH$_3$, —CH((OOCR$^{4\prime}$)CH$_3$, —CH(halo)CH$_3$, or —CH(halo)CH$_2$(halo), wherein $R^{4\prime}$ is H, alkyl (1-6C) optionally substituted with a hydrophilic substituent, or wherein $R^4$ is an organic group of <12C resulting from direct or indirect derivatization of vinyl, or wherein $R^4$ is a group containing 1-3 tetrapyrrole-type nuclei of the formula —L—P as herein defined.

In general, the "porphyrin-type photosensitizers" useful in the conjugates of the invention contain a "tetrapyrrole-type nucleus." This nucleus is a four-ring system of the skeleton:

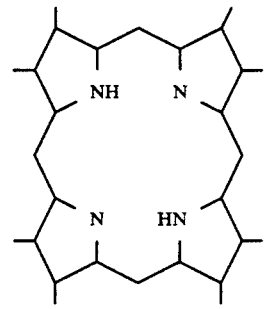

which is highly conjugate. It includes the porphyrin system, which is, in effect, a completely conjugated system, the chlorin system, which is, in effect, a dihydro form of the porphyrin, and the reduced chlorin system, which is a tetrahydro form of the completely conjugated system. When "porphyrin" is specified, the completely conjugated system is indicated; Gp is effectively a dihydro form of the porphyrin system.

When $R^4$ is —L—P, the substituent formula "—L—P" represents a substituent wherein —L— is selected from the group consisting of

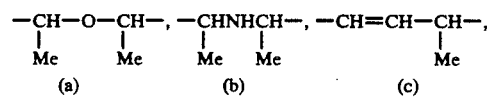

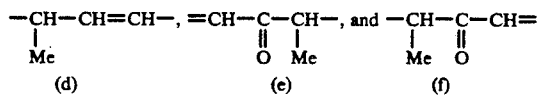

and P is a tetrapyrrole-type nucleus as above described.

The "P" to which L is attached can further be derivatized to additional tetrapyrrole-type nuclei as their $R^4$-corresponding substituent so as to form, for example, trimers.

It is understood that when —L— is of the formula (e) or (f), the ring system to which the double bond is attached will have a resonance system corresponding to

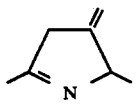

in the ring to which the double bond is attached, as shown.

Thus, the "porphyrin-type" photosensitizer is defined as any photosensitizing compound which contains sufficient conjugation in the tetrapyrrole ring system as described above to absorb an effective amount of light in the visible or near-ultraviolet region to become photoactivated. The unassigned bonds have various substituents as is generally known in the art and as described above.

Other Active Agents

While the above-described photosensitizers constitute a preferred group of active agents, other active agents, i.e., "drugs" may be advantageously substituted, if desired.

The term "drug" or "active agent" as used herein is intended to mean a compound or composition of matter which, when administered to an organism (human or animal) induces a desired pharmacologic and/or physiologic effect by local and/or systemic action. In general, the terms include the therapeutic or prophylactic agents in all major therapeutic/prophylactic areas of medicine. Examples of drugs useful in conjunction with the present invention include: anti-infectives such as antibiotics and antiviral agents; analgesics and analgesic combinations; anorexics; antihelminthics; antiarthritics; antiasthmatic agents; anticholinergic agents; anticonvulsants; antidepressants; antidiabetic agents; antidiarrheals; antihistamines; anti-inflammatory agents, antimigraine preparations; anti-motion sickness drugs; antinauseants; antineoplastics; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; steroids; hypnotics; immunosuppressives; muscle relaxants; parasympatholytics; psychostimulants; sedatives; and tranquilizers.

The Hydrophilic Polymer Carrier

The hydrophilic polymer to which the photosensitizing porphyrin-type compound is conjugated is generally an addition or condensation polymer with multiple functionality to permit the conjugation described. The functional groups ordinarily found on the porphyrin-type photosensitizers are common oxygen or nitrogen containing substituents; targeting agents often also contain —SH groups. Accordingly the functionality of the carrier must be compatible with these.

The characteristics required by the polymeric carrier are the following. First, one of the purposes of the carrier is to confer water solubility on the photosensitizing drug and/or targeting agent. Therefore, the carrier itself must be soluble. Typically, polymers which contain large numbers of heteroatoms are water soluble provided the molecular weights are not too high. For example, for the PVA preferred embodiment, molecular weights of less than 10 kd, preferably less than 8 kd are preferred. The molecular weight upper limit will, of course, vary with the nature of the polymer carrier used; however, for most generally water soluble polymers, the foregoing represent reasonable approximations.

Second, the carrier is preferably capable of conjugation to a multiplicity of moieties, both photosensitizing moieties and targeting agents. Therefore, the carrier to be used in the composition should have a multiplicity of functional groups which can be used per se, or which can be derivatized to other intermediate linkers to effect the covalent association of the photosensitizing drug and, if desired, the targeting agent. Suitable functional groups for such conjugation include hydroxyl groups, sulfhydryl groups, amino groups, carboxyl groups, aldehyde groups, and the like. Some of these are preferable to others because of their ability to resist participation in unwanted side reactions—for example, hydroxyl groups are preferred because compared, for example, to aldehyde groups, they are substantially less reactive.

One class of polymers which is useful in the conjugates of the invention comprise the polysaccharide polymers. Low molecular weight polysaccharides such as dextran, sepharose, or polyribose, polyxylose, and the like make suitable carriers.

Another class of preferred polymers are those which result from the addition polymerization of substituted ethylene or butadiene type monomers, including short chain unsaturated monomers such as propylene, wherein these monomers have substituents which are hydrophilic groups or can be derivatized to hydrophilic groups. Suitable hydrophilic groups which may be attached to the ethylene include hydroxy, carboxy and the esters or amides thereof, amines, and the like. If acrylic acid monomers are used (of the formula $CH_2CHR=CHCOOH$) the acid can be derivatized to suitable reactive groups prior to or subsequent to polymerization. Thus, for example, the ester formed from ethylene glycol and acrylic acid provides a hydroxyl group for derivatization to the photosensitizer. Polyallyl amines and alcohols are useful in the invention; a particularly preferred polymer is polyvinyl alcohol (PVA).

The molecular weight of the polymer is arbitrary, but generally the polymers forming the conjugates of the invention must have sufficient monomeric units so that there hydrophilicity is not destroyed when certain of the functional groups are reacted with the photosensitizer. Thus, a minimum number of units of approximately ten is preferred. The upper limit of molecular weight is determinable by solubility characteristics and varies greatly with the nature of the polymer chosen, as set forth above.

In addition to utilizing polymers derived from a single monomer, mixed polymers may also be employed. In this case, the hydrophilicity may be provided by a nonreactive component such as polyethylene glycol which is then further polymerized to monomers which bear the appropriate functional groups for reaction with the photosensitizer. Thus, for example, a copolymer of polyethylene glycol with polyvinyl alcohol containing 10-100 units of each is a convenient embodiment.

Targeting Agents

One of the major advantages of the solubilizing polymeric carriers of the invention is that they provide matrices whereby multiplicities of components can be bound to the carrier independent of each other and the activity of the individual components is thereby preserved. In particular, the invention includes conjugates wherein, in addition to the photosensitizing drug, specific targeting agents are coupled. In utilizing this approach, the photosensitizing activity of the drug is retained and the targeting agent does not suffer significant loss of activity.

The most commonly employed targeting agents are those which bind specifically to surface markers of cells of tissues to which the photosensitizing drug is to be directed.

For example, an immunoglobulin or portion thereof or a ligand specific for receptor can be used as a target specific component. The immunoglobulin can be polyclonal or monoclonal antibody and may comprise whole antibodies or immunologically reactive fragments of these antibodies such as $F(ab')_2$, Fab, or Fab' fragments. Use of such immunologically reactive fragments as substitutes for whole antibodies is well known in the art. See, for example, Spiegelberg, H. L., in "Immunoassays in the Clinical Laboratory" (1978) 3:1–23.

The ligand specific for receptor will be a moiety which binds a receptor at cell surfaces, and thus contains contours and charge patterns which are complementary to those of the receptor. A variety of cell types have specific receptors designed to bind hormones, growth factors, or neurotransmitters, and these ligands specific for receptor are included as well as synthetic materials which bind specifically to a receptor. Examples of such ligands include the steroid hormones, such as progesterone, estrogens, androgens, and the adrenal cortical hormones; growth factors, such as epidermal growth factor, nerve growth factor, fibroblast growth factor, and so forth; other protein hormones, such as human growth hormone, parathyroid hormone, and so forth; and neurotransmitters, such as acetylcholine, serotonin, and dopamine, as well as analogs of these substances which bind receptors.

Preparation of the Conjugates

The conjugates of the invention comprise the above-described hydrophilic polymer coupled with a drug such as a porphyrin-type sensitizing drug. They may further contain a targeting agent as described in the previous section. Methods for forming these conjugates are commonly practiced and a variety of approaches may be used depending on the nature of the polymer chosen, the nature of the functional groups available in the photosensitizer, and the approach chosen for conjugation of the targeting agent. In some instances, it may be useful to provide spacing between the immediate polymer backbone and the functional group to be covalently linked to photosensitizer or targeting agent. For example, 1,6-diaminohexane can be used as a spacer, as illustrated below. Generally, however, the spacer contains two functional groups at either end of an inert backbone, and a wide variety of such spacers is available in the art. The only requirements for the spacer are a functionality capable of binding the functionality on the hydrophilic polymer and a functionality capable of binding to the photosensitizer or targeting agents.

In providing the conjugates of the invention, a multiplicity of drug moieties is conjugated to the polymer; typically the range is 500:1 to 1:1 of photosensitizer:carrier. Preferred are ratios of 75:1–10:1, 10:1 is especially preferred. Preferred ratios of target specific component to carrier are 5:1 to 1:1, preferably 3:1 to 2:1.

Thus, depending on the nature of the functional groups used to conjugate the photosensitizer and optionally the targeting agent, a variety of conjugation techniques can be used. General means to conjugate the functionalities of the attached moieties and the hydrophilic polymer carrier will be known to those of ordinary skill in the art. In addition to direct conjugation, bifunctional linkers can be used, such as the diamine illustrated below, aldehydes such as glutaraldehyde, or other homobifunctional linkers, as well as commercially available more complex homo- and heterobifunctional linkers such as those manufactured by Pierce Chemical Company, Rockford, Ill. The types of conjugation linkages used can include formation of disulfides, addition of sulfhydryls to pi-bonds, formation of amides, esters, hydrazones, and the like.

Taken generally, this invention provides a pharmaceutical composition comprising as an active ingredient a hydrophilic, water-soluble, multifunctional carrier with which is conjugated an active agent. In some preferred embodiments this active agent is a photosensitizer. In other preferred embodiments, this carrier is additionally conjugated with one or more target specific components. In this description, wherein the polymer, target compositions, various linking groups, spacers, and methodologies of preparation and use are set forth with specific reference to photosensitizers, these teachings can be adapted and applied generally to active agents as a whole.

The target specific component-containing products of this invention can be characterized as including: polymer carrier and active agent in 1:1 to 500:1 molecular ratio of agent:polymer, especially 10:1 to 75:1 and target specific component in a 1:1 to 25:1 and especially 1:1 to 5:1 molecular ratio of target specific component:polymer.

These materials can be formed by the general process of conjugating an active agent or active agent precursor to a first portion, which is some but not all, of the present or potential reactive sites on a hydrophilic water-soluble polymer, and conjugating a target-directing group or component to a second portion of the reactive sites present in the polymer.

As has been set forth, this proportional conjugating can be carried out by controlling the conditions of the first conjugating to not involve all the sites on the polymer; or it can be carried out by temporarily blocking, and thus temporarily "reserving" a portion of the sites prior to and through the first conjugating, or it can be carried out by providing a plurality of types of reactive sites on the polymer and using one type of site for conjugating to the active agent and another for conjugating to the target-directing group.

In a particularly preferred method for obtaining coupling of the carrier to a carboxyl containing drug, a carrier which contains a multiplicity of hydroxyl functional groups is first derivatized to an electrophile that effectively converts the hydroxyls to leaving groups. In general, if only the drug is to be coupled to carrier, essentially all or any desired portion of the hydroxyls may be so converted. If it is desired to further couple the carrier to a targeting agent, for example, or to another moiety, less than all of the available hydroxyls will be thus converted.

For the conversion of the hydroxyl functionalities, the carrier is dissolved in DMSO and treated with base in the presence of the electrophile donor. A particularly suitable electrophile donor is 2-fluoro-1-methyl-pyridinium toluene-4-sulfonate (FMP). Other suitable donors include tosyl moieties. The thus derivatized carrier is then reacted in the presence of a suitable reducing agent with an alkylene diamine of a desired length to distance the drug to be coupled from the carrier surface. Typical alkylene diamines contain two amino groups separated by 4–8 methylenes. Particularly preferred is 1,6-hexane diamine.

The reducing agent is added to the reaction mixture in approximately equimolar quantities to the alkylene diamine to prepare the alkylene diamine-derivatized carrier. The resulting carrier thus has free amino groups for coupling to the carboxyl-bearing drug; this further coupling can be conducted by a variety of conventional means including providing conditions in the presence of dehydrating agents such as dicyclohexyl carbodiimide or EDCI.

Alternatively, the free amino groups on the alkylene diamine-derivatized carrier may be reacted with any functional group contained in the pharmaceutically-active ingredient compatible with reaction to the amine. Additionally, heterobifunctional linkers containing a moiety reactive with the amino group and an additional functional moiety reactive with a functional group on the drug can be used so that essentially any functional group-bearing drug can be coupled to the carrier using this technique.

Additional Components

In addition to the required photosensitizer and hydrophilic backbone, certain additional components may be coupled to the conjugate. These include label, additional cytotoxins and other functionalities which may be useful in the applications herein.

The conjugates of the invention may be further derivatized to a compound or ion which is a label. A wide variety of labeling moieties can be used, including radioisotopes, chromophores, and fluorescent labels. Radioisotope labeling in particular can be readily detected in vivo. Radioisotopes may be coupled by coordination as cations in the porphyrin system. Useful cations include technetium, gallium, and indium. In the conjugates, either the porphyrin or the polymer can be linked to or associated with label.

In general, the conjugates can also be administered or used in in vitro methods when complexed to appropriate metal ions. As is generally understood in the art, the tetrapyrrole-type nucleus can be treated with an appropriate ion such as magnesium ion, zinc ion, stannous ion, and the like to obtain the metal complex. As stated above, the metal ion may also be a radiolabel. The nature and desirability of the inclusion of a metal ion in the tetrapyrrole-type nucleus depends on the specific application for which the conjugate is intended. When the inclusion of a metal ion is desired, the desired metal ion can be inserted using the appropriate metal salts under known conditions. For example, zinc ion can be introduced by treating the compound with zinc acetate in 1:1 methylene chloride:methanol.

Administration and Use

The conjugates of the invention are thus useful in general, in the manner known in the art for hematoporphyrin derivative and for DHE. These materials are useful in sensitizing neoplastic cells or other abnormal tissue to destruction by irradiation either in vivo or ex vivo using visible light—upon photoactivation, the photosensitizer has no direct effect, nor it is entered into any biological event; however the energy of photoactivation is believed to be transferred to endogenous oxygen to convert it to singlet oxygen. This singlet oxygen is thought to be responsible for the cytotoxic effect. In addition, the photoactivated forms of porphyrin fluoresce, which fluorescence can aid in localizing tumors or other sites to which the conjugates home.

Typical indications, known in the art, include destruction of tumor tissue in solid tumors, dissolution of plaques in blood vessels (see, e.g., U.S. Pat. No. 4,512,762); treatment of topical conditions such as acne, athlete's foot, warts, papilloma, and psoriasis and treatment of biological products (such as blood for transfusion) for infectious agents, since the presence of a membrane in such agents promotes the accumulation of the drug.

The conjugates of the inventions are formulated into final pharmaceutical compositions for administration to the subject or applied to an in vitro target using techniques known in the art generally. A summary of such pharmaceutical compositions may be found, for example, in *Remington's Pharmaceutical Sciences*, Mack Publishing Co., Easton, Penna., latest edition.

The conjugates can be used in the systemic treatment of tumors and neoplastics made as bronchial, cervical, esophageal or colon cancer and for the diagnosis of same. They can be administered systemically, in particular by injection, or can be used topically. They can be used singly or as components of mixtures.

Injection may be intravenous, subcutaneous, intramuscular, or even intraperitoneal. Injectables can be prepared in conventional forms, either as liquid solutions or suspensions, solid form suitable for solution or suspension in liquid prior to injection, or as emulsions. Suitable excipients are, for example, water, saline, dextrose, glycerol and the like. Of course, these compositions may also contain minor amounts of nontoxic, auxiliary substances such as wetting or emulsifying agents, pH buffering agents and so forth.

Systemic administration can also be implemented through implantation of a slow release or sustained release system, by suppository, or, if properly formulated, orally. Formulations for these modes of administration are well known in the art, and a summary of such methods may be found, for example, in *Remington's Pharmaceutical Sciences* (supra).

For diagnosis, the conjugates may be used alone or may be labeled with a radioisotope or other detecting means.

If treatment is to be localized, such as for the treatment of superficial tumors or skin disorders, the active conjugates may be topically administered using standard topical compositions involving lotions, suspension, or pastes.

The quantity of conjugate to be administered depends on the choice of active ingredient, the condition to be treated, the mode of administration, the individual subject, and the judgment of the practitioner. Depending on the specificity of the preparation, smaller or larger doses may be needed. For compositions which are highly specific to target tissues, such as those which include a highly specific monoclonal immunoglobulin preparation or specific receptor ligand, dosages in the range of 0.05–1 mg/kg are suggested. For compositions which are less specific to the target tissue, larger doses, up to 1–10 mg/kg may be needed. The foregoing ranges are merely suggestive, as the number of variables in regard to an individual treatment regime is large and considerable excursions from these recommended values are expected.

The wavelength of irradiating light is preferably chosen to match the maximum absorbance of the porphyrin-type photosensitizer. For BPD-MA and BPD-DA, the preferable wavelength is between about 680 and 700 nm. The suitable wavelength for any of the photosensitizers can readily be determined from its absorption spectrum. Preferred irradiation dosages are in the range of 50–500 J cm$^{-2}$, and preferred irradiation dosage rates are in the range of 100–300 mW cm$^{-2}$.

In addition to in vivo use, the conjugates of the invention can be used in the treatment of materials in vitro to destroy harmful viruses or infectious agents. For example, blood plasma or blood which is to be used for transfusion or banked for future transfusion can be treated with the compounds of the invention and irradiated to effect sterilization. In addition, biological products such as Factor VIII which are prepared from biological fluids can be irradiated in the presence of the conjugates to destroy contaminants.

EXAMPLES

The following examples are intended to illustrate the invention but not to limit its scope.

EXAMPLE 1

Preparation of PVA/Photosensitizer Conjugates

Figures 1, 2:
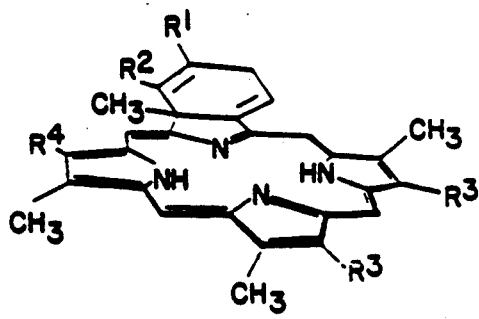
Figures 1, 2, 3:
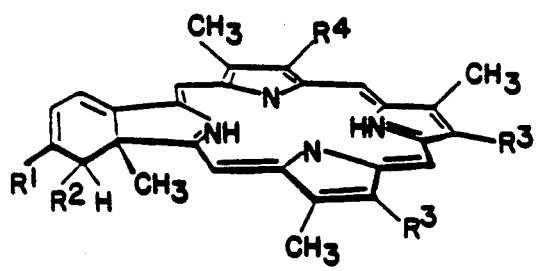
Figures 1, 2, 3, 4:
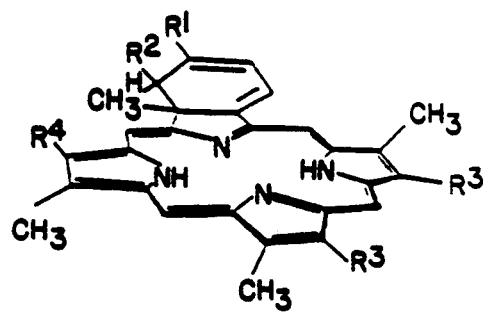
Figures 1, 2, 3, 4, 5:
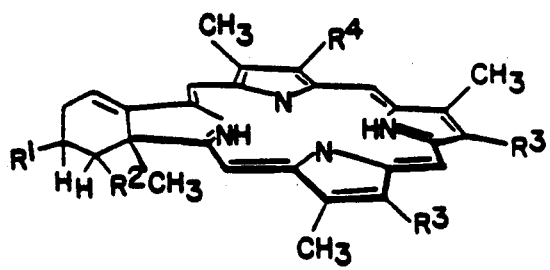

Two photosensitizers were used for conjugation to polyvinyl alcohol (PVA). A DHE mixture was obtained as the commercially available Photofrin® II from Quadralogic Technologies Inc., Vancouver, B.C. As described above, this is the mixture obtained when hematoporphyrin derivative is treated as described in U.S. Pat. 4,649,151. The other is designated BPD-MA which is the compound of formula 3 wherein $R^1$ and $R^2$ are carbomethoxy, $R^4$ is CHCH$_2$ and one $R^3$ is 2-carbomethoxy ethyl and the other $R^3$ is 2-carboxy ethyl. The compound is supplied as a mixture of the two isomers having a single hydrolyzed $R^3$ The procedure for conjugation is outlined in FIG. 2.

Polyvinyl alcohol was supplied as an 88% hydrolyzed 10,000 molecular weight polymer purchased from Aldrich Chemical Company, Milwaukee, Wis. Thus, the PVA contains slightly more than 200 units.

To conjugate the photosensitizers with PVA, the alcohol groups were modified to provide amino reactive groups as follows: a complex was formed between pyridine and 2-fluoro-1-methylpyridinium toluene-4-sulfonate (FMP) by adding 5 ml pyridine to 916 mg (3.23 mmol) FMP and stirring for 5 minutes. Polyvinyl alcohol (323 mg, 32.3 umol) was dissolved in 2 ml anhydrous dimethylsulfoxide (DMSO). The PVA solution was transferred to the reaction flask containing the FMP-pyridine complex, and the mixture was stirred for another two hours at ambient temperature.

To the PVA-FMP intermediate, 431 mg (3.71 mmol) of 1,6-hexane diamine was added and stirred for one hour. The crude product was dialyzed (MW cutoff 12 kd-14 kd) in 4 liters of distilled water (four changes). The modified PVA conjugate (M-PVA) was lyophilized and 700 mg of solid brown powder was obtained. The M-PVA prepared according to this protocol contained about 60% substitution of OH groups by hexane diamine.

BPD-MA (supra) (21 mg, 26.8 mmol) and 50 mg (260.8 mmol) of 1-ethyl-3-(3-dimethylaminopropyl) carbodiimide (EDCI) were mixed in 10.5 ml anhydrous DMSO and stirred for 30 minutes at room temperature under argon. The mixture was divided into 5 portions of 0.5, 1, 2, 3 and 4 ml. To each portion, 1 mg modified PVA in 1 ml anhydrous DMSO was added and the mixtures were stirred for 24 hours at room temperature under argon. The reactions were monitored by using TLC techniques and quenched with 2 ml distilled water. The preparations were then dialyzed against distilled water at 4° C., and the concentration of photosensitizer in the conjugates was analyzed spectrophotometrically. The ratios were estimated at 100:1, 75:1, 50:1, 25:1, and 12:1, respectively, BPD-MA to M-PVA. By suitable adjustment of proportions, varying amounts of BPD-MA can be coupled to the polymer. All reactions and handling were in the dark, and the final solutions were lyophilized. Conjugates can readily be separated from unreacted BPD-MA chromatographically. Reaction yields were more than 95%. The final products were kept in Drierite at 4° C. in the dark.

Similarly, DHE was treated with M-PVA to produce conjugates with ratios of 50:1, 25:1, 12:1 of DHE to M-PVA.

To test stability, the conjugates were dissolved in pH 4.21, 7.26 and 8.42 buffers at 0.064 mM and stored at various temperatures: $-20°$ C., 4° C., 20° C. and 37° C. TLC analysis was used to monitor any dissociation; only the conjugate maintained at pH 8.42 at 37° C. showed dissociation at 4 weeks. After this period, slight dissociation was observed in all preparations.

Figure 3A:
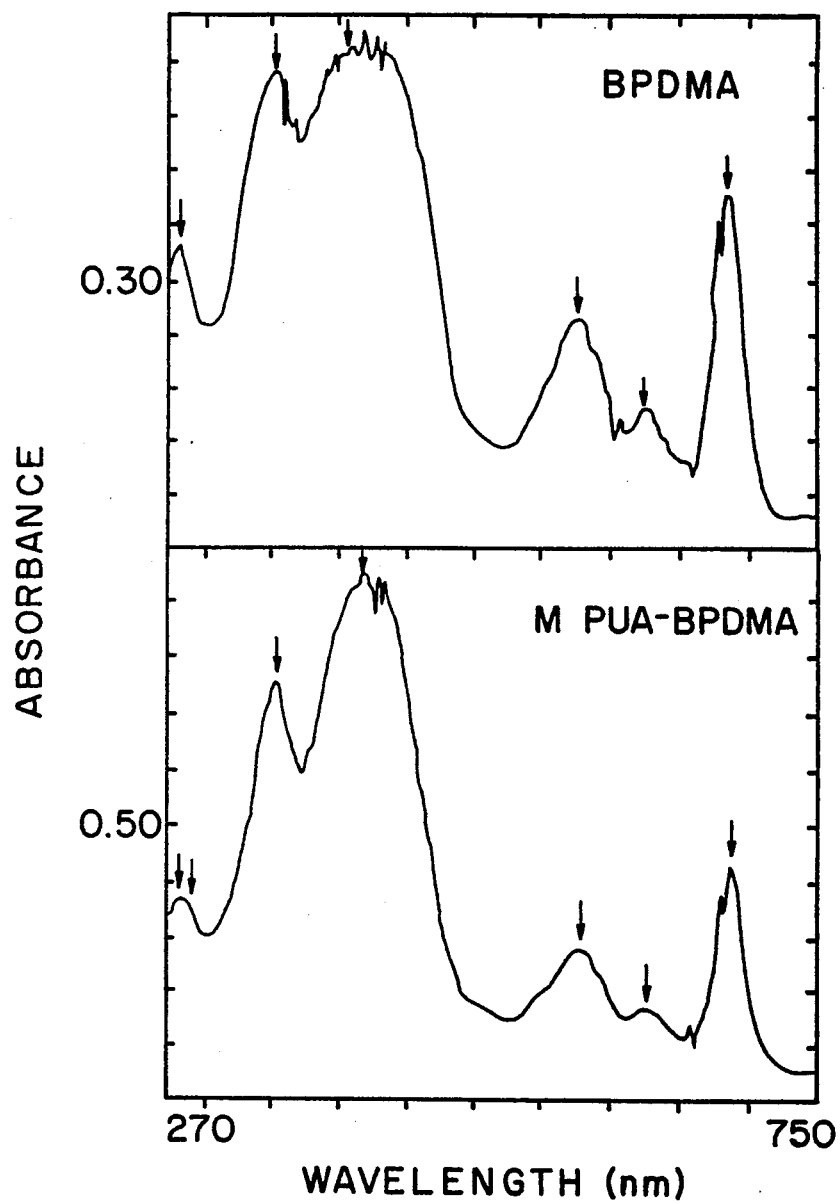
FIGS. 3A and 3B show comparative spectra of conjugated and unconjugated photosensitizers of the invention.
Figure 3B:
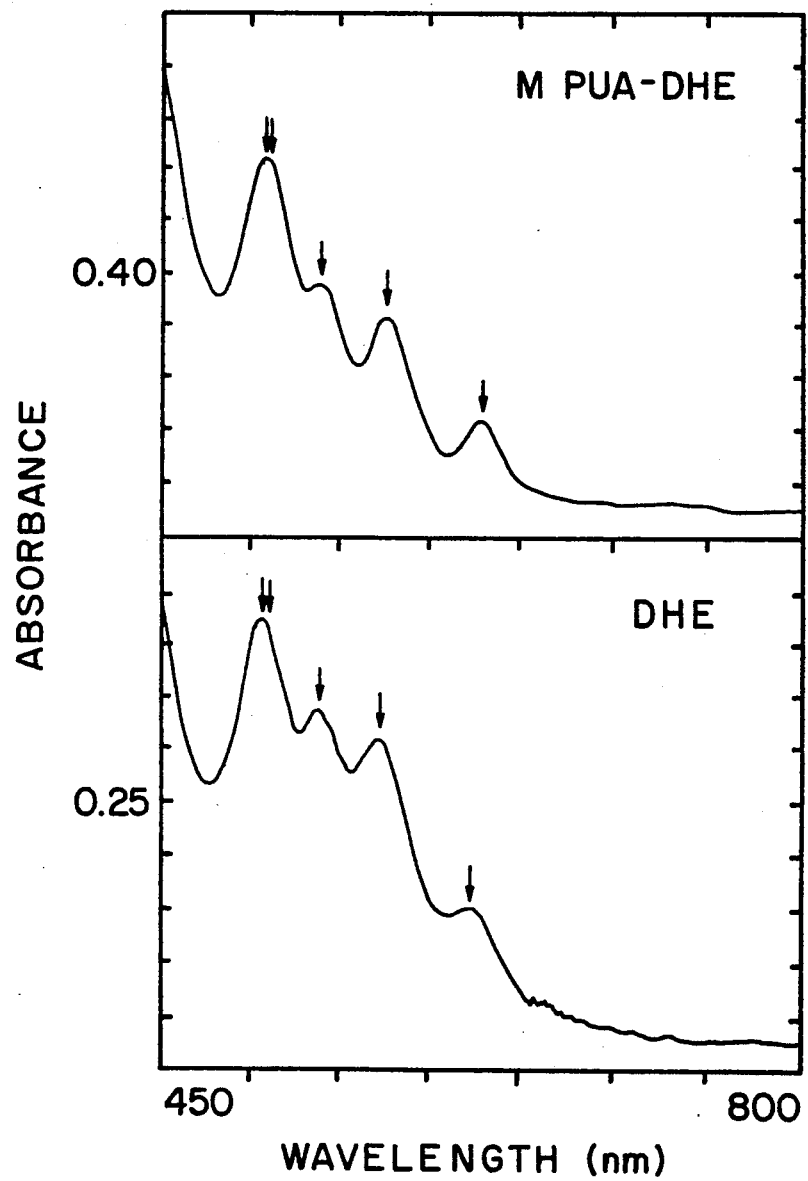

FIGS. 3A and 3B show comparative spectra of conjugated and unconjugated BPD-MA and DHE, respectively. No significant changes are noted.

EXAMPLE 2

Cytotoxcity of the Conjugates

Adherent human lung cancer cell lines A549 and A431 were grown to log phase and cells were harvested with 10% trypsin and vigorous agitation. A final concentration of $10^6$ cells/ml were plated (100 ul) into 96 well Immulon II plates and incubated overnight. On each plate, standard concentrations of DHE, BPD-MA, or the respective conjugates dissolved in MEM plus 5% FCS were tested in triplicate. Controls of cells not exposed to porphyrin were run on each plate.

The kinetics of cytotoxicity were explored by varying the exposure times of the cells to porphyrins from 15 minutes to 18 hours depending on the specific experiment. The porphyrins were washed from the microtiter wells with MEM plus 5% FCS maintained at 37° C. The wells were then filled with 100 ul medium and were exposed to 300–750 nm light (5.4 Joules/cm$^2$) for one hour. The cells were replaced in a 10% CO$_2$ humidified incubator and allowed to recover for one hour. Cell viability was determined using an MTT assay (Mosmann, T., *J Immunol Methods* (1983) 65:55–63). The percentage killed was calculated for each porphyrin concentration, and the LD of the cell line determined. The results of this assay are shown in FIGS. 4A–4C.

Figure 4A:
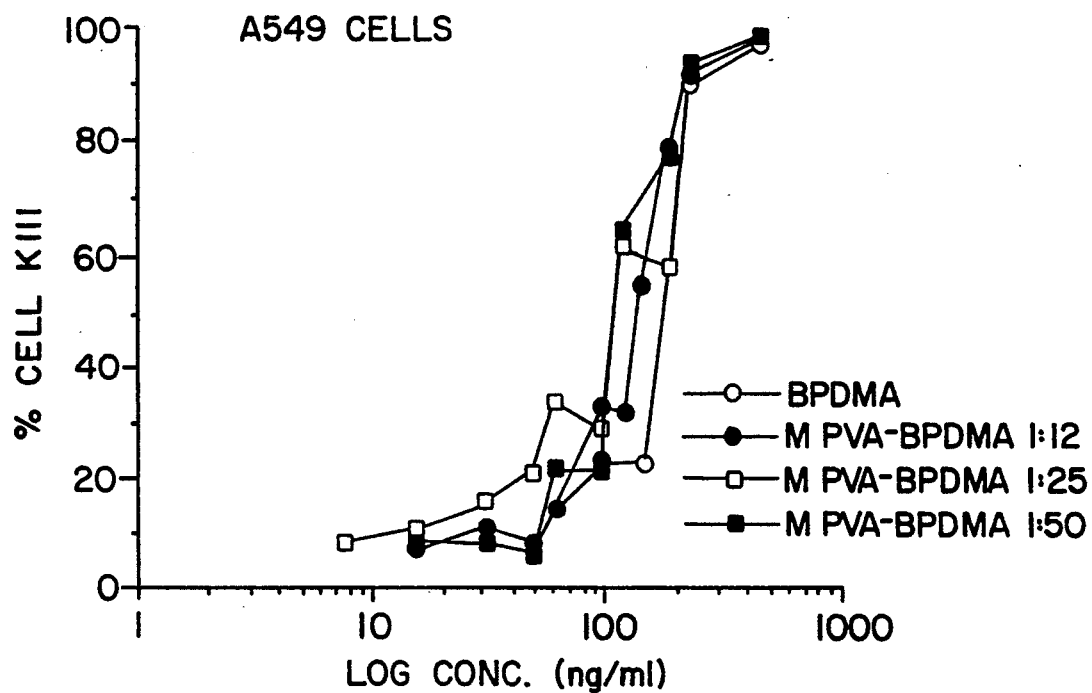
FIGS. 4A, 4B and 4C show comparisons of the cytotoxicity of the conjugated and unconjugated photosensitizers of the invention using BPD-MA or DHE conjugates on A549 and A431 cells.
Figure 4B:
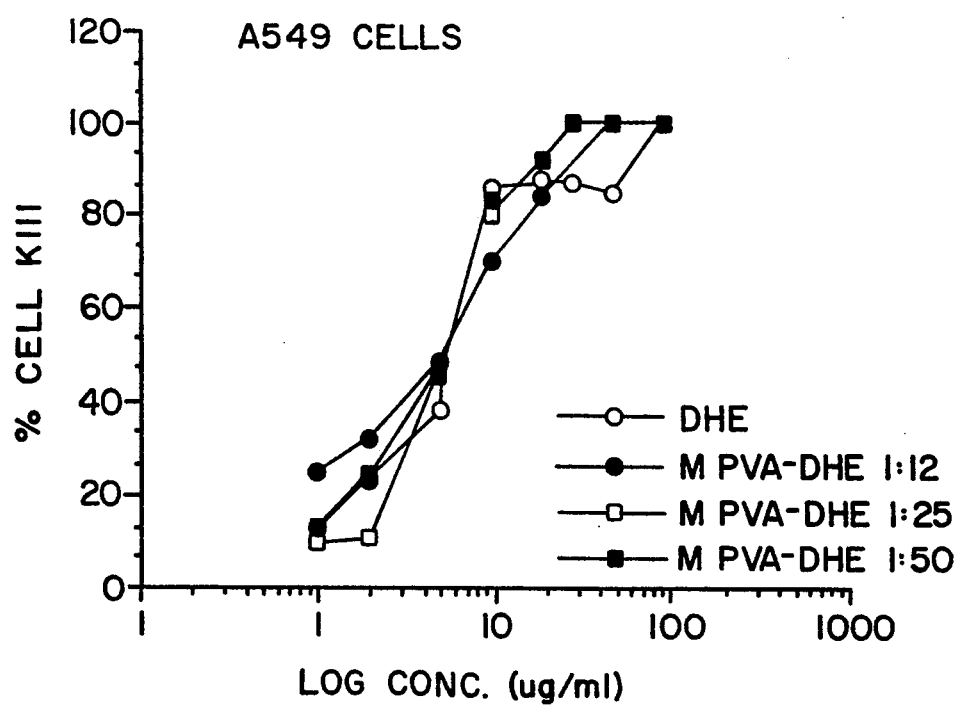
Figure 4C:
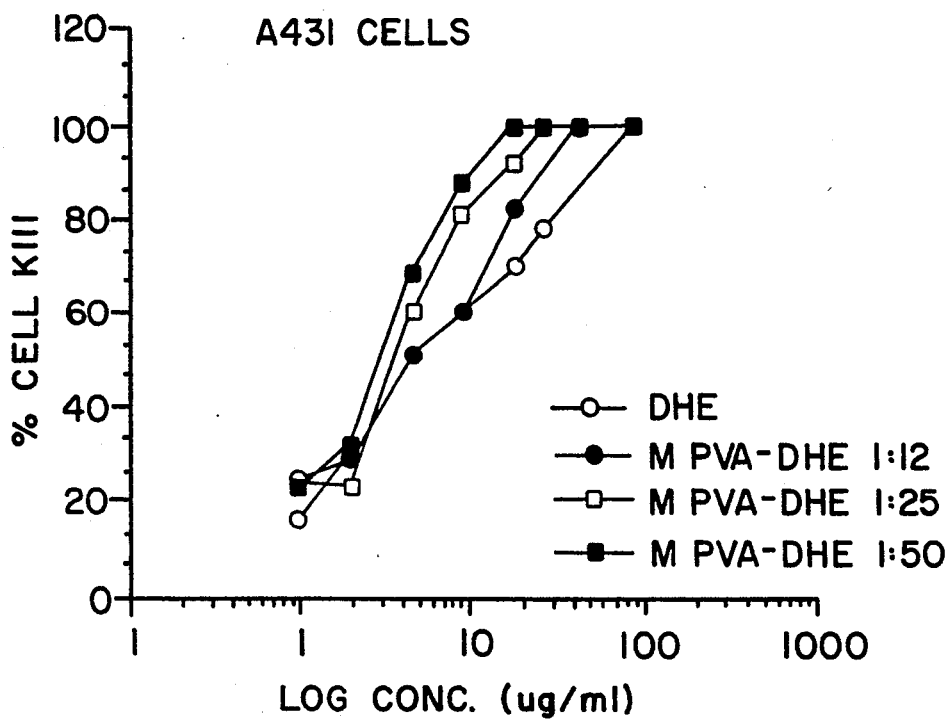

FIG. 4A shows these results for BPD-MA both alone and in conjugates of various ratios using A549 cells in the test. FIG. 4B shows an analogous determination on A549 cells using DHE both in unconjugated form and conjugated to the modified PVA at various levels. FIG. 4C shows analogous results for the DHE and its conjugates using A431 cells in the assay. As shown, there are no significant differences in the phototoxicity of the porphyrins alone compared to the conjugated materials. No significant differences between various ratios between 12:1 and 50:1 were found.

Figure 4D:
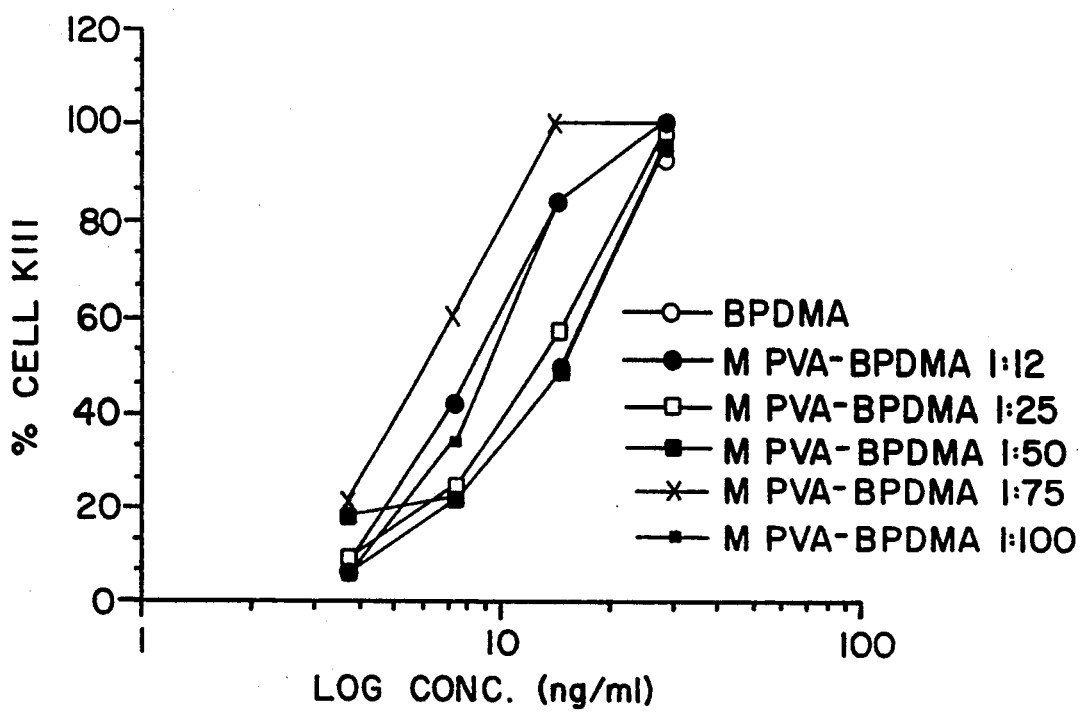
FIG. 4D shows a comparison of the cytotoxicity of the conjugated and unconjugated photosensitizers of the invention using BPD-MA on P815 cells.

Similarly, a nonadherent murine mastocytoma cell line, P815, described by Richter, A. M., et al., *J Nat'l Cancer Inst* (1987) 79:1327-1331, was used as a cytotoxicity test subject. Cells in log phase were incubated for one hour at 37° C. with a range of either BPD-MA alone or BPD-MA conjugate in the absence of serum. Following incubation, cells were washed and exposed to fluorescent light (a bank of four fluorescent tubes—G.E. F20T12 cool white Delux as described by Richter (supra) for one hour (5.4 J/cm$^2$). The cells were then incubated overnight in DME plus 5% FCS at 37° C. Survival of cells was assessed by MTT assay 18 hours after light irradiation. The results are shown in FIG. 4D. There were no significant differences between the porphyrin and the conjugate in phototoxicity, although it appears that the conjugate is slightly more effective.

EXAMPLE 3

Biodistribution of the Conjugates

Figure 5A:
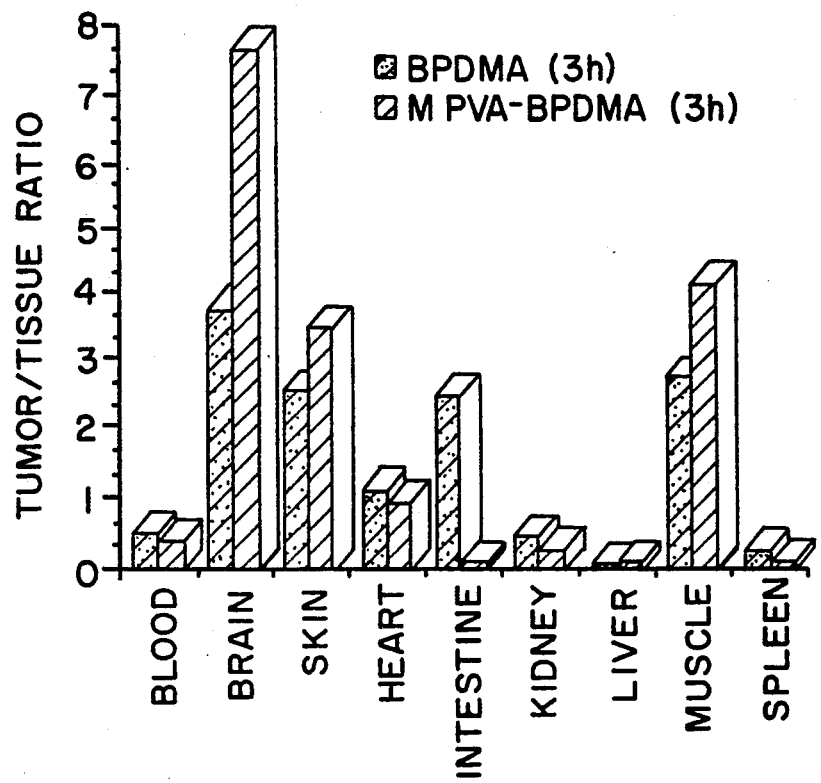
FIGS. 5A and 5B show a comparison of the biodistribution of the conjugated and unconjugated forms of the photosensitizing drugs after 3 hours and 24 hours, respectively.
Figure 5B:
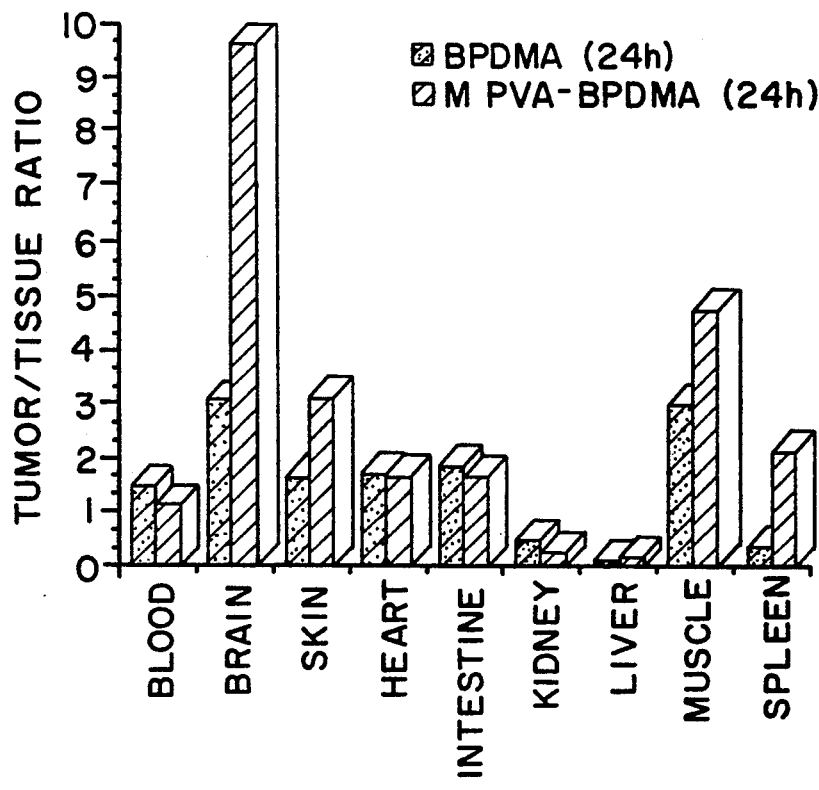
Figure 6:
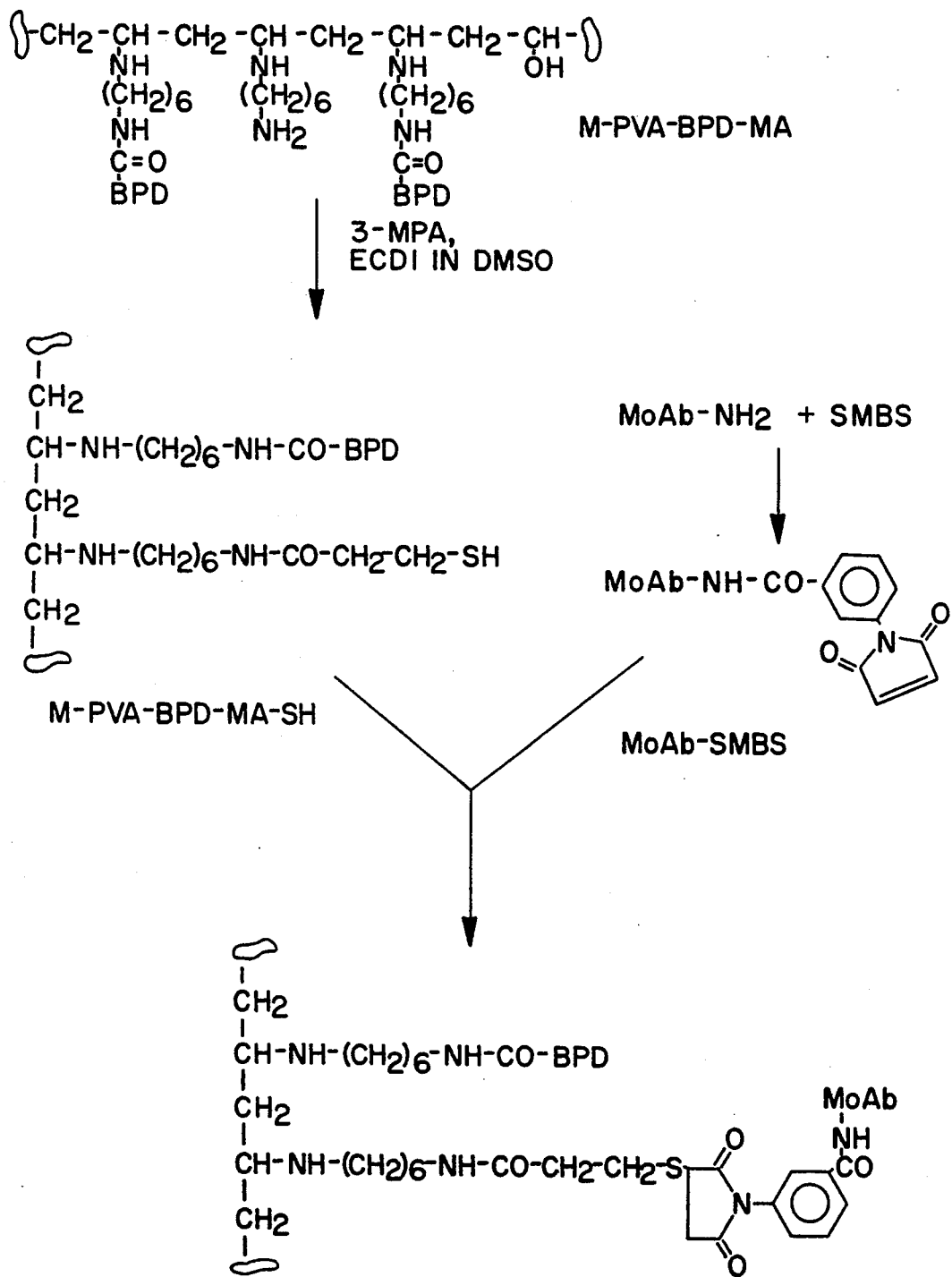

A preparation of BPD-MA/M-PVA at a 25:1 ratio was prepared as described in Example 1 using tritiated BPD-MA and used to follow biodistribution of this conjugate in DBA/2 mice bearing subcutaneous P815 tumors. The procedure is described in Richter, A. M., et al., *J Photochem Photobiol* (1989). Briefly, $1\times10^5$ P815 cells were injected subcutaneously in the right flank. Fifteen days later, when the tumors were 8-12 mm in diameter, the mice were injected intravenously with a 0.2 ml containing 12.4 ug of BPD-MA or the PVA conjugate containing an equivalent amount of BPD, a specific activity of 5.56 uCi/mg. The animals were sacrificed at 3, 24 and 48 hours post-injection and various tissues were removed to determine biodistribution. The results of this study are shown in FIG. 5A for 3 hours and 5B for 24 hours.

Both the conjugate and the BPD-MA alone show high tumor/tissue ratios in various organs, especially in muscle and brain. The conjugate is fairly consistently superior to the unconjugated BPD-MA in tumor specificity.

EXAMPLE 4

Preparation of Target-Specific Conjugates

Figures 1, 2, 3, 4, 5, 6:
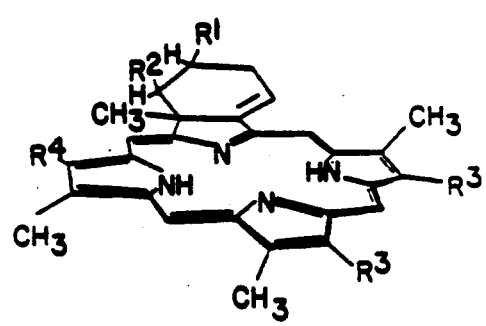
Figure 2:
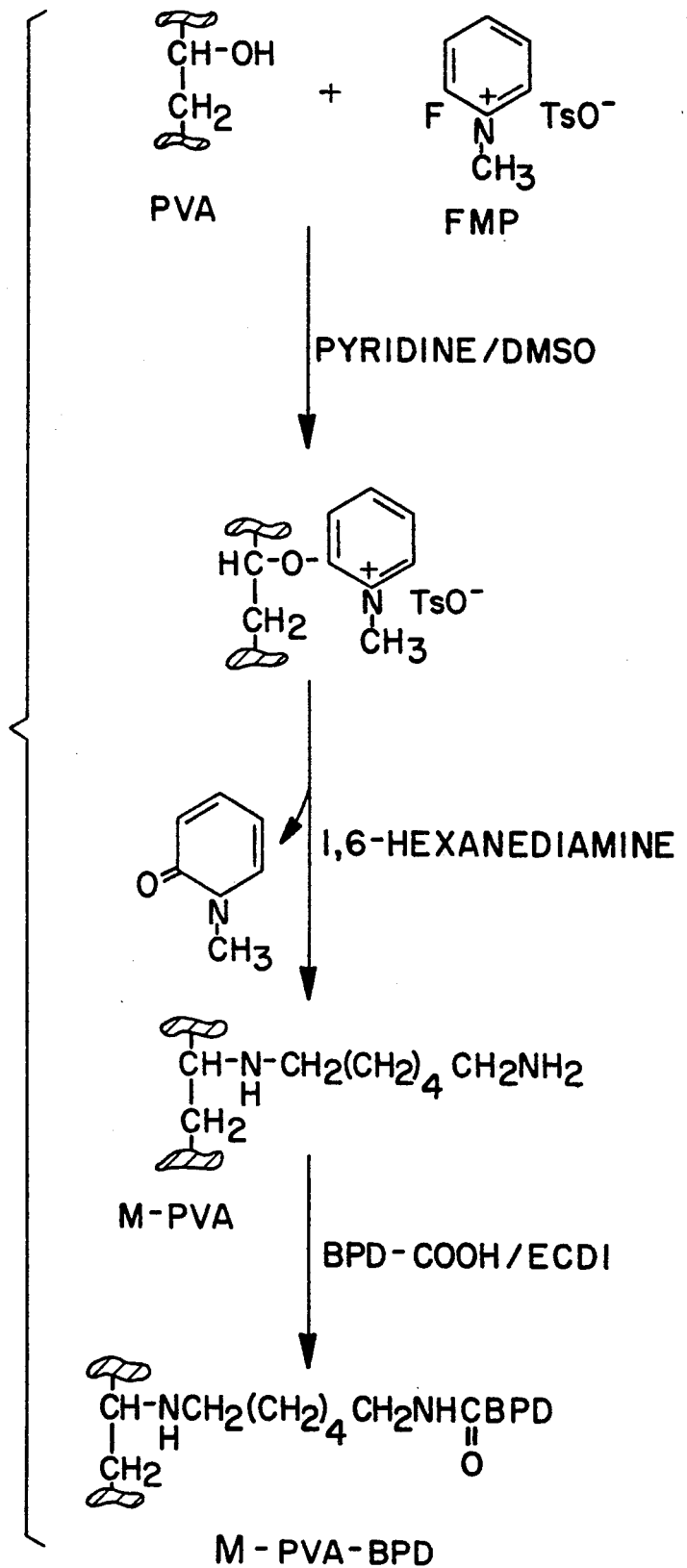

A conjugate of BPD-MA with PVA having a ratio of BPD:PVA of 25:1 was prepared using the PVA described in Example 1 and the methodology set forth therein. The conjugate was then reacted with 3-mercaptopropionic acid in the presence of ECDI in DMSO to obtain a product having the mercapto-containing acid moiety contained at 2-3 reactive sulfhydryls per carrier molecule. The sulfhydryl-derivatized conjugate was then treated with the monoclonal antibody T48, specific for human chorionic gonadotropin which had been conjugated to the commercially available heterobifunctional linker, sulfo-M-maleimidobenzoyl-N-hydroxysulfosuccinimide ester (SMBS, Pierce Chemical Company, Rockford, Ill.). The maleimide moiety reacts directly with the sulfhydryl group to obtain a linked conjugate through a thioether bond to the linker. The steps in this procedure are outlined in FIG. 6.

In more detail, preliminary experiments established that molar ratios of 10:1 for the 3-mercaptopropionic acid (MPA):M-PVA-BPD-MA in the reaction mixture resulted in the introduction of 3-4 thiol groups per carrier molecule; higher ratios of 3-MPA did not significantly increase the level of thiol group introduction. Thus, the M-PVA-BPD-MA was reacted with 3-MPA at a ratio of 1:10 in the presence of 0.8M EDCI in DMSO. The reaction was stirred for 4 hours at room temperature under argon, and then dialyzed against 0.01 M acetate buffer, pH 5.5.

The monoclonal antibody T48 at 9.615 mg/ml was dialyzed against 0.01 M carbonate buffer, pH 8.5; SMBS was added to this buffer in a 30-fold molar excess. The mixture was stirred for two hours after which it was washed through centricon-30 and the buffer was changed to 0.01 M acetate, pH 5.5.

The T48-SMBS conjugate and the M-PVA-BPD-MA were mixed in equimolar concentrations in 0.01 M acetate buffer, pH 5.5, stirring gently for 18 hours at 4° C. The resulting conjugate was concentrated by dialysis against polyethylene glycol.

Figure 7:
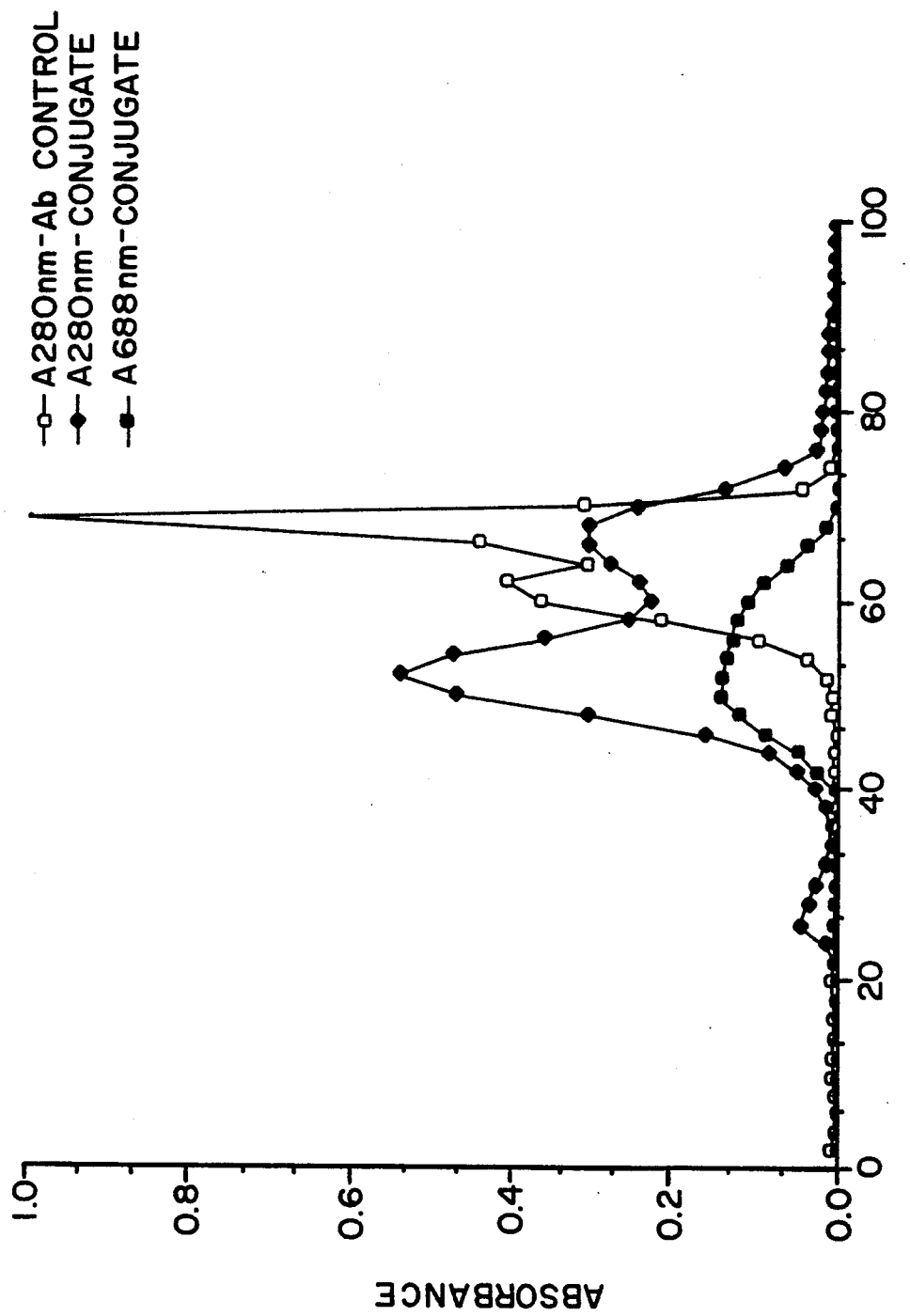
FIG. 7 shows an elution profile of a conjugate of the invention which includes BPD-MA and monoclonal antibody T48 both conjugated to carrier.

The resulting conjugates containing both the T48 antibody and the BPD-MA photosensitizer were recovered from the reaction mixture and chromatographed on Sepharose CL-4B. The concentrated samples were made up to 0.5% w/v 2,000 MW PVA for application to the column to prevent unwanted adsorption of the conjugate, and then applied in 1 ml portions to a column of bed volume 68.4 ml, equilibrated with 01 M acetate buffer, pH 5.5. Application of the buffer to the column was continued at a rate of 0.43 ml/minute and fractions of 2 ml were collected and analyzed at both 280 nm and 688 nm using an LKB Ultraspectrophotometer 4050. The elution pattern is shown in FIG. 7. As the pattern shows, the conjugated material elutes as a defined peak at an elution volume of approximately 50 ml. Covalent binding of the T48 to the carrier system was confirmed using SDS-PAGE.

EXAMPLE 5

Activity of Target-Specific Conjugates

The eluted, purified conjugates were then assayed for ability of the antibody to bind antigen and for the cytotoxicity with respect to M1 cells as compared to the free antibody or photosensitizer.

To determine the specific activity of the T48 antibody, Immulon II ELISA plates were coated with human chorionic gonadotropin (HCG) antigen at 5 ug/ml in a volume of 100 ul per well in 0.1 M bicarbonate buffer, pH 9.6. Test samples containing T48 in conjugated and unconjugated form were added in serial dilutions to the wells, and plates were developed with alkaline phosphatase labeled rabbit-antimouse Ig obtained from Jackson Immunoresearch Lab. The substrate for the enzyme label was p-nitrophenylphosphate and plates were read at 405 nm on a standard plate reader.

Figure 8:
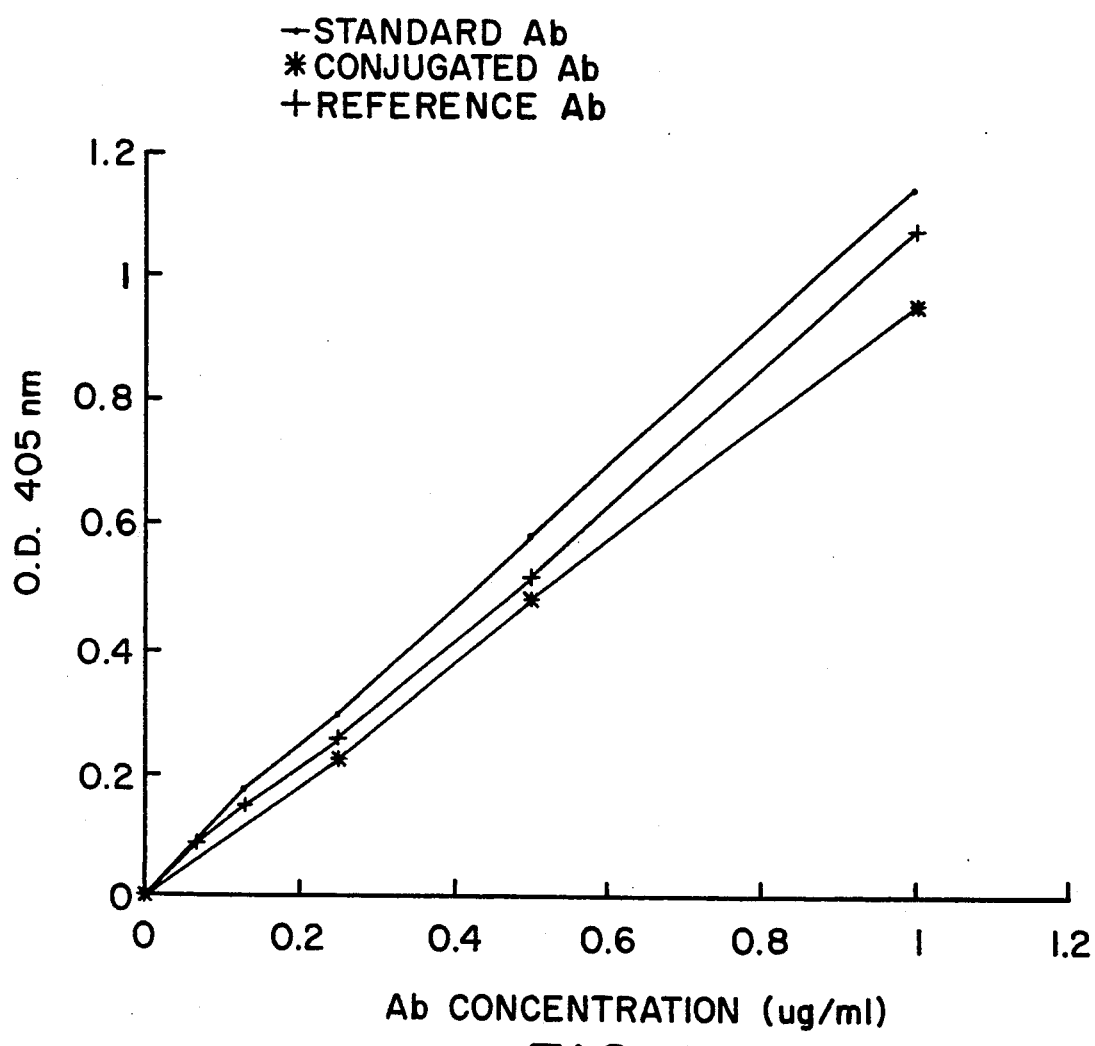
FIG. 8 shows the retention of immunoreactive activity by T48 antibody in the conjugates of the invention.

The results of an ELISA assay showing the binding of conjugate to antigen in comparison to unconjugated antibody are shown in FIG. 8. As shown in FIG. 8, the concentration curve for the conjugated antibody tracked that of the antibody in unconjugated form. In these curves, the starting concentration was 1 ug/ml and a two-fold dilution series was used.

Figure 9:
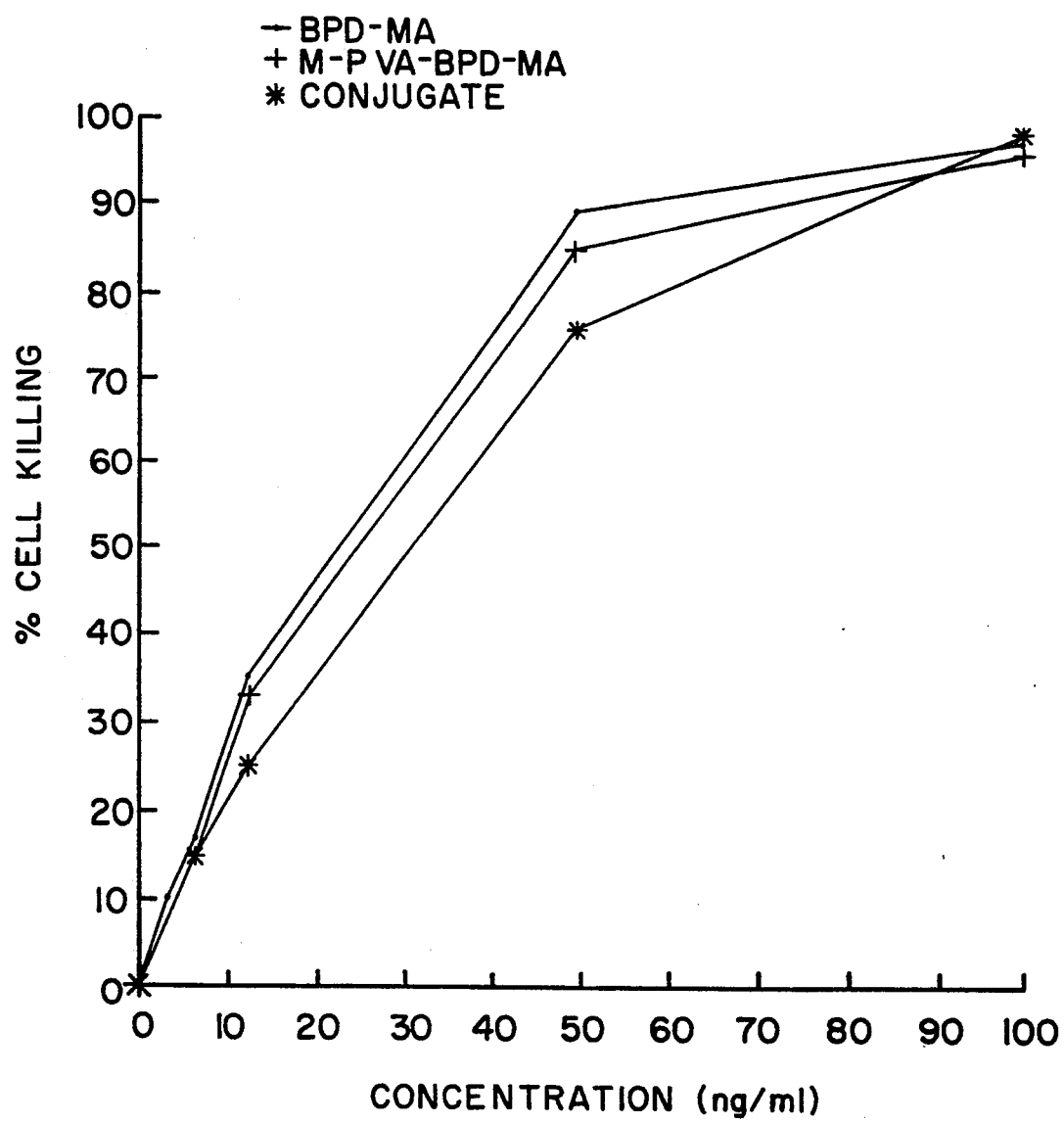
FIG. 9 shows the cytotoxicity of the BPD-MA conjugated to carrier.

The cytotoxicity assays were conducted as described by Richter, A. M., et al. (1979) *J. Nat,l Cancer Inst.* 79:1327-1332. Briefly, M-1 tumor cells, in single cell suspension, obtained from a freshly prepared excised subcutaneously grown tumor were plated in 96 well Falcon plate in 200 ug DME (Gibco) containing 10% FCS at a concentration of $10^5$ cells/well. After 24 hours, the culture medium was changed, and at 48 hours, the cells were washed and then incubated with various concentrations of BPD-MA, with M-PVA-BPD-MA and with the antibody-M-PVA-BPD-MVA conjugate for 1 hour at 37° C., in the dark, in the absence of serum. Following the incubation, cells were exposed to light for one hour (4 Joules/$cm^2$) and then incubated further in DME-5% FCS at 37° C., in the dark, in a $CO_2$ humidified incubator, for 18 hours. At that time, the viability of the cells was tested using MTT (3-(4,5(dimethylthiazol-2-yl)-2,5-diphenyltetrazolium) bromide as described by Mossmann, T., *J Immunol Methods* (1983) 65:55–63. The percentage killing was calculated for each test material and the of the cell line was determined. The results are shown in FIG. 9. Again, the ability of the photosensitizing drug to effect cell killing was substantially unaffected by its conjugation to either modified PVA per se or the conjugate containing target-specific agent.

EXAMPLE 6

Preparation and Testing of Additional Tarqet-Specific Conjugate

A conjugate of BPD-MA was formed with PVA and this conjugate subsequently conjugated to 5E8 monoclonal antibody to yield a target-specific conjugate.

Monoclonal Antibodies. The 5E8 monoclonal antibody reacts with a cell surface glycoprotein associated with human squamous cell carcinomas of the lung but not with normal lung tissue. The monoclonal antibody was purified from ascites fluid. The control, T48 (Quadra Logic Technologies, Vancouver, Canada), has specificity for another antigen, human chorionic-gonadotropic hormone (hcg, Sigma, St. Louis, Mo.).

Photosensitizer. The photosensitizer (BPD) was used. Tritiated BPD was obtained from New England Nuclear.

Cell Lines. The A549 cell line (22), derived from a human squamous cell carcinoma, was obtained from the ATCC, maintained according to recommended procedures, and was used as the target cell. The M-1 cell line is a rhabdomyosarcoma from DBA/2 mice. A549 cells were maintained in MEM (Terry Fox Lab, Vancouver, Canada) containing nonessential amino acids in Eagle's balanced salt solution. M-1 cells were maintained in DME (GIBCO, Grand Island, N.Y.). Both media were supplemented with L-glutamine and 10% FCS. Both cell lines were stored in 5% $CO_2$ incubator.

Conjugation Procedures. The procedures used for producing immunoconjugates involved the formation initially of conjugating BPD to a hydrophilic carrier, modified polyvinyl alcohol (PVA, Aldrich Chemical Co., Milwaukee, Wis.) substantially as shown in Example 1 and FIG. 2. Briefly, PVA (MW ca 10,000) was reacted with 1,6-hexanediamine so that approximately 40% of the hydroxyl groups of PVA were substituted to provide free amino groups for further substitutions. This modified PVA is readily amenable to reaction with the free carboxyl group of BPD, in the presence of carbodiimide. We have found that PVA-BPD conjugates with varying PVA:BPD ratios could easily be produced by altering molar ratios. In the present example molar ratios of PVA:BPD were 1:25 in all cases. The PVA-BPD carrier system was further substituted with 3-mercaptopropionic acid (3-MPA, Aldrich Chemical Co.) such that about three free thiol groups were introduced per carrier molecule. Carbodiimide was also used to carry out this step. This carrier system (PVA-BPD-SH) can be prepared and characterized in bulk and then used for conjugation with a variety of monoclonal antibodies using the heterobifunctional linker sulfo-M-maleimidobenzoyl-N-hydroxysulfosuccinimide ester (SMBS, Pierce, Rockford, Ill). SMBS was reacted with the antibody in question by mixing at a molar ratio of 30:1 (SMBS:MoAb) in carbonate buffer, pH 8.5. This resulted in the presence of 2–3 SMBS groups being bound per molecule of antibody. Final conjugation between the PVA-BPD-SH carrier system and the MoAb was effected by mixing the two reactants at a 1:1 molar ratio in acetate buffer, pH 5.5.

Separation of Conjugates by Gel Filtration. The conjugated product was separated from unconjugated reactants by passage of the material over a Sepharose CL-4B (Pharmacia LKB, Uppsala, Sweden) column. Eluted material was monitored for absorbance at 688 (to detect BPD) and 280 nm (to detect protein). The peak eluting at 15–27 ml contained both 688 and 280 nm absorbing material and preceded a peak which absorbed strongly only at 280 nm and eluted at 28–35 ml. This latter was shown to elute in the same position as free antibody. The material eluting at 15–27 ml was assumed to be conjugated and was collected and used for further testing.

SDS-PAGE Analysis of Unlabeled and Tritiated Conjugates. Material assumed to be conjugated and collected from Sepharose CL-4B columns was subjected to analysis by reducing SDS-PAGE to determine whether material containing protein and BPD were really covalently linked. Conditions for gel analyses were as follows: Sepharose CL-4B column-purified conjugated materials were subjected to SDS-PAGE analysis to determine whether material containing protein and BPD were really covalently linked. Samples containing either $^3$H-BPD-PVA-5E8 or unlabeled BPD-PVA-5E8 were run in parallel on a 7.5% polyacrylamide reducing gel. The gel was run 30 mA (constant current). After electrophoresis, gels were either silver stained or cut into 2 mm slices and transferred into scintillation vials containing 10 ml of 3% Protosol in Econofluor (New England Nuclear). Gel slices were allowed to soak in the above solution at 37° C. for 16–18 hr. Radioactivity was measured using a Beckman liquid scintillation counter (Beckman Instruments, Fullerton, Calif.).

Cytotoxicity Assays. Standard assays, described by Richter et al. *J Natl Cancer Inst* (1979) 79:1327–1332, were used to determine the phototoxicity of BPD throughout the conjugation procedures. Briefly, A549 and M-1 cells were grown to log phase and cells were harvested with 10% trypsin and vigorous agitation. Cells were then plated in 96-well Falcon plates in 200 ul DME (Gibco, Grand Island, N.Y.) containing 10% FCS (FCS, Sigma Chemical Co., St. Louis, Mo.) at a concentration of $10^5$ cells/well. Twenty-four hours later the culture medium was changed, and 48 hr later the cells were washed and then incubated with various concentrations of drugs for either 2 hr or 24 hr at 37° C. in the dark either in the presence or absence of serum. Following incubation, the cells were washed with PBS and replaced with fresh DME (serum-free). Then the cells were exposed to light for 1 hr (4 Joules/$cm^2$) and then incubated further in DME-5% FCS at 37° C. in the dark, in a $CO_2$ humidified incubator for 18 hr. At that time the viability of the cells was tested using MTT3-(4,5-dimethylthiazol-2,5-diphenyl-tetrazoliumbromide; Sigma) and percent killing calculated for each tested material by comparing values to appropriate dark controls (drug with no light). The light source used in this set of experiments consisted of a set of 16 100 W tungsten bulbs (General Electric; spectrum 400 to 1200 nm). The light was filtered through a 4 cm thick water filter filled with circulating cool water. The temperature at the plane of exposure did not exceed 22° C. The incident light density was 6 $mW/cm^2$ as measured by YSI Kettering Model 65 radiometer, and the dose delivered was $21.6J/cm^2$.

ELISA Assays. The 5E8 antibody reacts in a standard cellular ELISA with A549 cells. Briefly, A549 cells were grown to confluence in 96-well Falcon plates. Plates were then washed with PBS and the cells were fixed to the bottom of the wells with 0.25 glutaraldehyde for 2 hr. At that time the plate was quenched with PBS containing 1% BSA. After quenching, 5E8 and BPD-PVA-5E8 were tritiated over these plates. Plates were developed with alkaline phosphatase labeled rabbit anti-mouse Ig (Jackson Immuno Research Lab, Inc.) and the p-nitrophenyl phosphate substrate. Plates were read at 405 nm on a Titertek Multiskan plate reader (Flow Lab).

Figure 10:
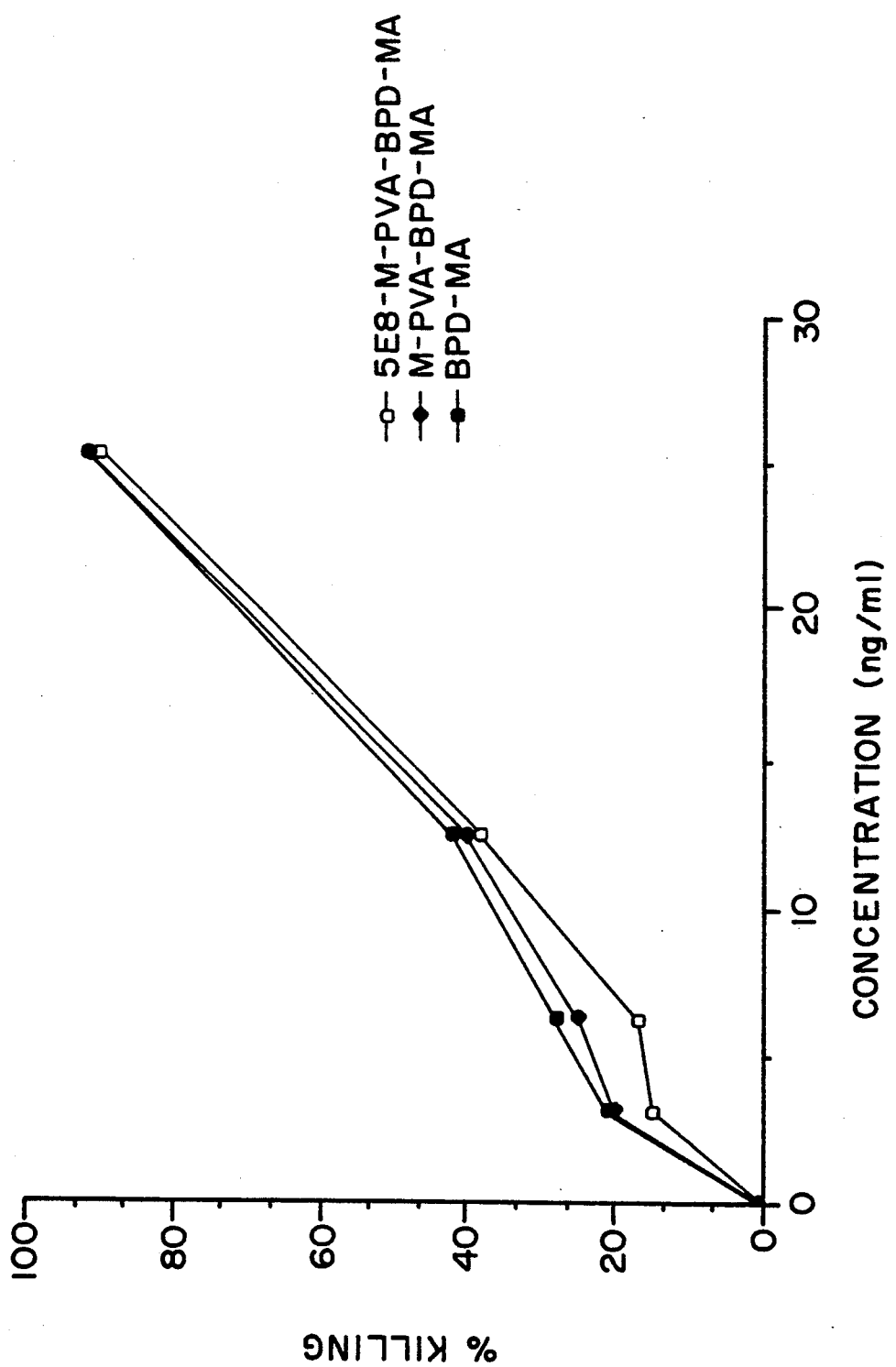
FIGS. 10-14 show the retention of activity and specificity of action of a representative drug, BPD-MA, conjugated to a carrier together with 5E8 monoclonal antibody targeting agent.

Specific activity of 5E8 conjugate was tested through a cellular ELISA and the results showed that 80% of activity was retained. The activity of the BPD associated with the 5E8 MoAb conjugate was determined using a standard cytotoxicity assay. The results (FIG. 10) showed that the 5E8-PVA-BPD conjugate was equally as effective in killing cells as was either free BPD or the PVA-BPD carrier.

Figure 11:
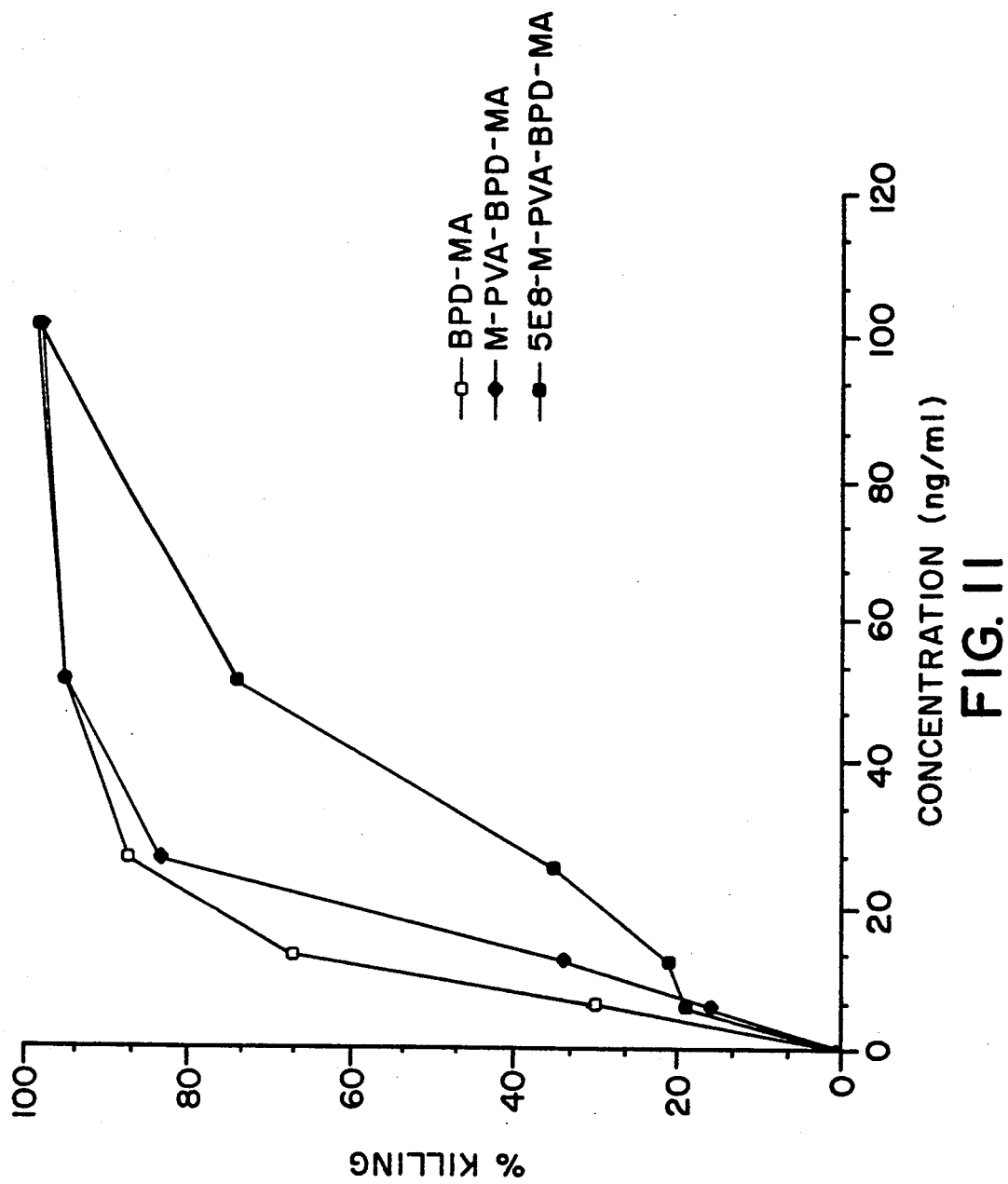
Figure 12:
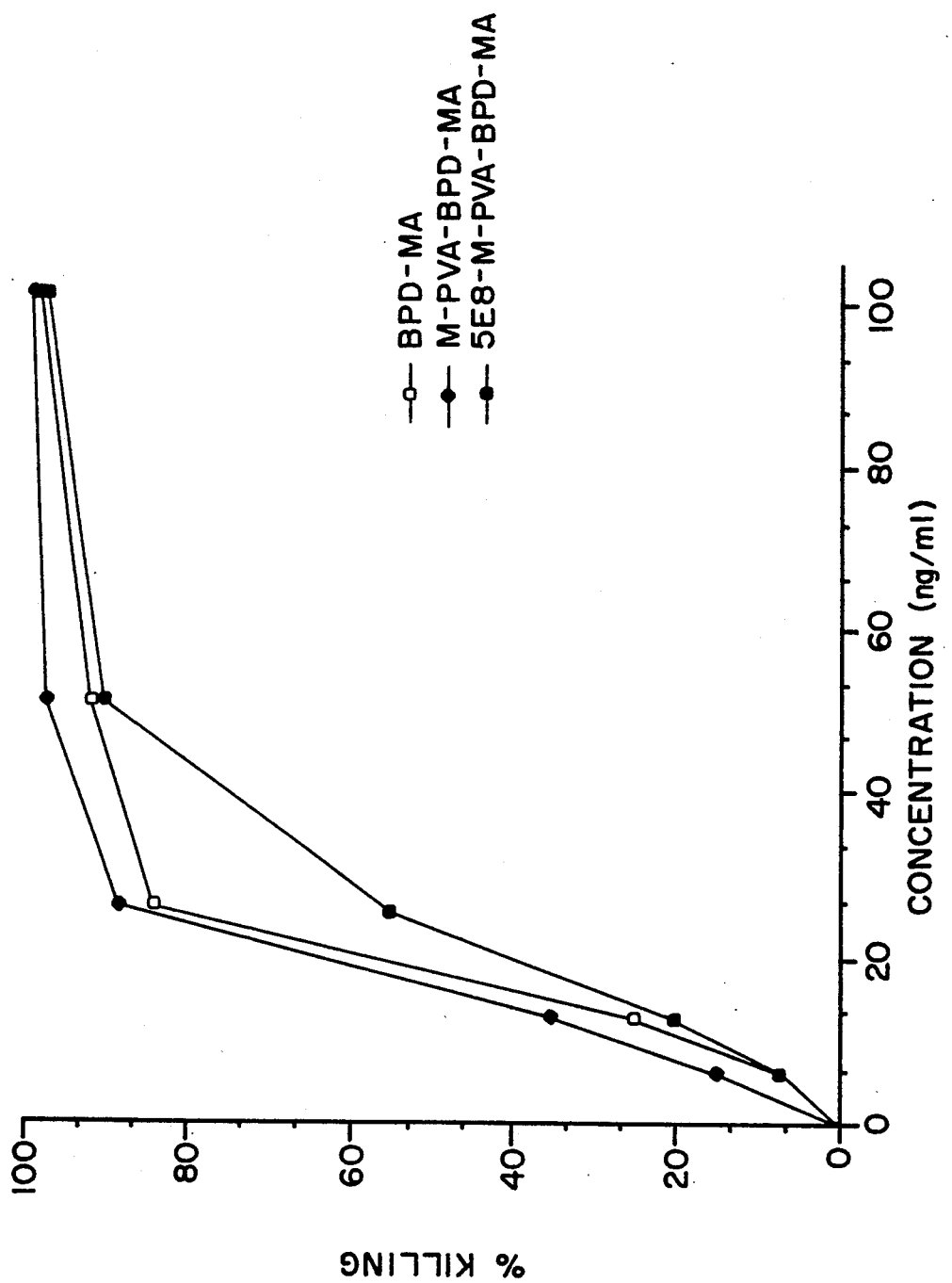
Figure 13:
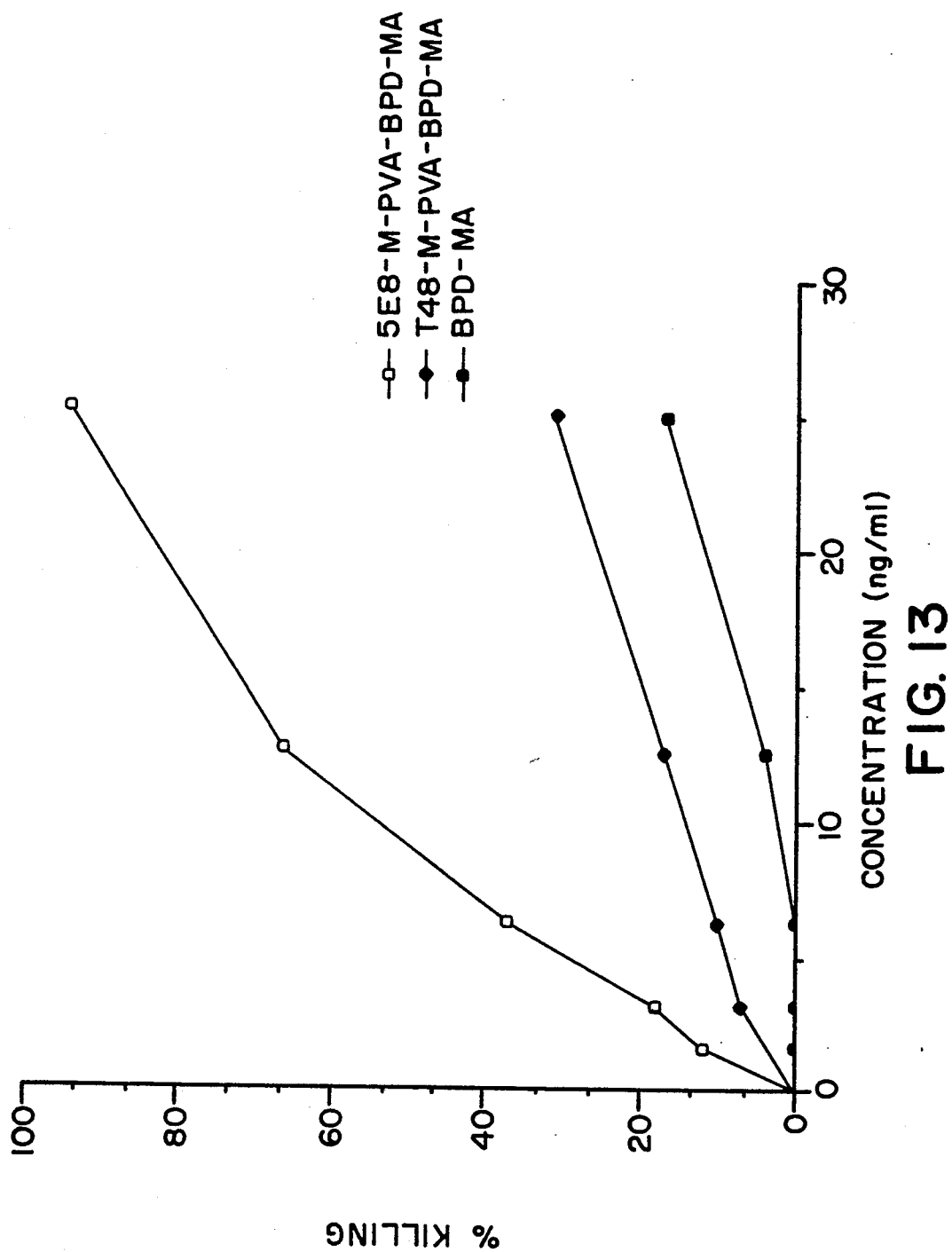
Figure 14:
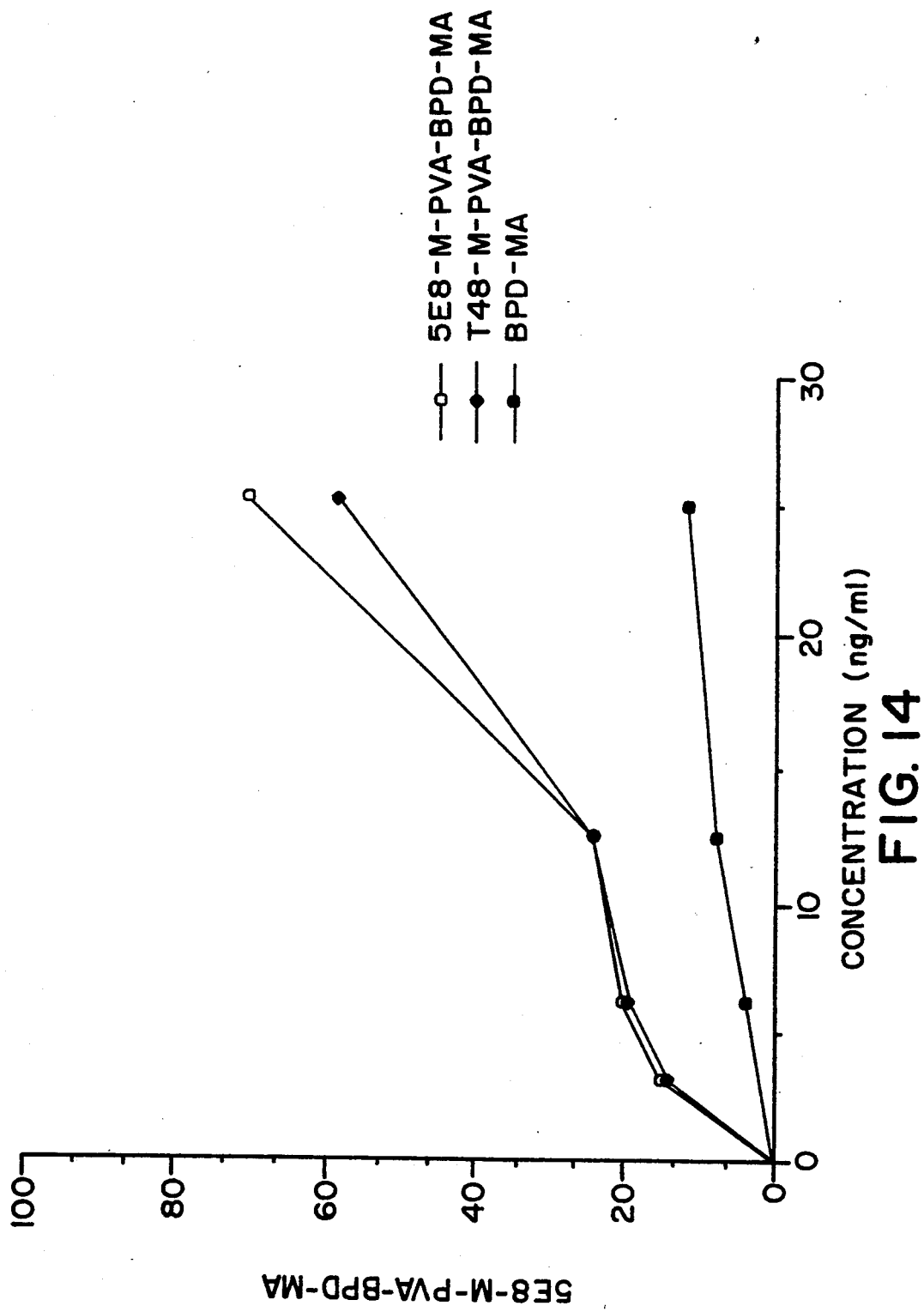

Further experiments were performed to determine whether 5E8-PVA-BPD conjugates would bestow enhanced delivery and phototoxicity to targeted cell lines. Initially, cytotoxicity for the A549 cell line was tested, using BPD alone, FVA-BPD or 5E8-PVA-BPD. Cells and photosensitizer preparations were mixed in the absence of serum and incubated for 2 hr in the dark prior to exposure to light. The results (FIG. 11) showed that under these conditions, the MoAb conjugate was taken up less well by the cells than either BPD on its own or PVA-BPD. This experiment was repeated, except that preincubation was continued for 24 hr. This prolonged incubation enhanced photoxic killing in all preparations but did not improve selectivity with the MoAb conjugate in comparison to other BPD preparations (FIG. 12). Similar experiments were carried out in the presence of 10% FCS. In one series (FIG. 13) A549 cells in 10% FCS were incubated in the dark for 2 hr with BPD, the 5E8 MoAb conjugate or the control T48 MoAb conjugate. Under these conditions it appeared that good selectivity was shown by the 5E8 conjugate in comparison to control materials. In order to establish specificity, a further experiment was carried out using M-1 cells in 10% FCS as targets (the 5E8 MoAb does not react with this murine cell line). The results (FIG. 14) show that there is no difference in phototoxicity between the conjugates (5E8 and the T48 control) indicating that the results of FIG. 14 do establish the specificity of the 5E8 conjugate. These data provide evidence that the 5E8 conjugate can, under the parameters described here, deliver photosensitizer in both a selective and specific manner, to the designated target cell and that the presence of serum enhances the specificity.

EXAMPLE 7

Preparation of a Derivatized PVA Intermediate 500 mg of polyvinyl alcohol (PVA) is stirred for one hour in the presence of 2 ml DMSO at room temperature to dissolve the PVA. To this is added 0.5% ml triethylamine and the mixture is incubated for 30 minutes, followed by addition of 1.416 g of FMP (5 mmol). The mixture is stirred for two hours at room temperature before adding 4 g of 1,6-hexanediamine. The mixture is then stirred overnight, followed by the addition of 946 mg (25 mmol) of sodium borohydride. The reaction mixture is again incubated for one hour and an excess of water is added to quench the reaction. The mixture is dialyzed against water overnight and product is recovered from the dialyzate.

What is claimed is:

1. A method to prepare a conjugate of a pharmaceutically active compound with a hydrophilic, water-soluble, multifunctional polymeric carrier, said carrier having a multiplicity of hydroxy substituents, which method comprises:
    contacting said carrier with a molar excess of an electrophile donor effective to convert said hydroxyl moieties to leaving groups; followed by
    treating said carrier having said converted hydroxyls with an alkylene diamine in the presence of a metal hydride reducing agent in approximately equimolar amount to the alkylene diamine to obtain an alkylene diamine-derivatized carrier; followed by
    coupling said alkylene diamine-derivatized carrier with a pharmaceutically active compound containing carboxyl substituents to obtain a pharmaceutically active conjugate of said carrier with said active compound.

2. The method of claim 1 wherein said pharmaceutically active compound is a green porphyrin.

3. The method of claim 1 wherein said hydrophilic water-soluble multifunctional carrier is polyvinyl alcohol.

4. The method of claim 1 wherein said electrophile donor is 2-fluoro-1-methylpyridinium toluene-4-sulfonate (FMP).

5. The method of claim 1 wherein said reducing agent is sodium borohydride.

6. The method of claim 1 wherein said reducing agent is sodium borohydride.

7. The method of claim 1 wherein the hydrophilic, water-soluble, multifunctional carrier is polyvinyl alcohol; the electrophile donor is 2-fluoro-1-methylpyridiniumtoluene-4-sulfonate; and wherein said pharmaceutically active compound is a porphyrin-type photosensitizer.

8. The method of claim 7 wherein said porphyrin-type photosensitizer is a green porphyrin.

* * * * *